(12) United States Patent (10) Patent No.: US 8,748,112 B2
Stylianou (45) Date of Patent: Jun. 10, 2014

(54) METHODS OF DETERMINING CANCER CELL RESPONSIVENESS TO A NOTCH INHIBITORY AGENT

(75) Inventor: Spyros Stylianou, Nicosia (CY)

(73) Assignee: Trojan Technologies, Ltd., London (GB)

( * ) Notice: Subject to any disclaimer, the term of this patent is extended or adjusted under 35 U.S.C. 154(b) by 0 days.

(21) Appl. No.: 13/399,556

(22) Filed: Feb. 17, 2012

(65) Prior Publication Data

US 2013/0022966 A1   Jan. 24, 2013

Related U.S. Application Data

(62) Division of application No. 12/245,518, filed on Oct. 3, 2008, now Pat. No. 8,119,366.

(60) Provisional application No. 61/044,215, filed on Apr. 11, 2008, provisional application No. 60/978,039, filed on Oct. 5, 2007.

(51) Int. Cl.
*G01N 33/53* (2006.01)
*G01N 33/566* (2006.01)
*G01N 33/00* (2006.01)
*C07K 14/435* (2006.01)

(52) U.S. Cl.
USPC ............... 435/7.2; 435/7.23; 530/350; 800/3

(58) Field of Classification Search
CPC ............. G01N 33/15; G01N 33/5005; G01N 33/5008; G01N 33/5011; G01N 33/6872; C07K 14/435; C07K 14/4702
See application file for complete search history.

(56) References Cited

U.S. PATENT DOCUMENTS

| 2002/0052308 A1 | 5/2002 | Rosen et al. |
| 2005/0232927 A1 | 10/2005 | Clarke et al. |
| 2007/0060743 A1 | 3/2007 | Tang et al. |

FOREIGN PATENT DOCUMENTS

| WO | WO 99/11809 A1 | 3/1999 |
| WO | WO 02/083179 A2 | 10/2002 |
| WO | WO 02/096952 A2 | 12/2002 |
| WO | WO 02/098465 A3 | 12/2002 |
| WO | WO 03/102242 A1 | 12/2003 |
| WO | WO 2006/037462 A2 | 4/2006 |
| WO | WO-2006092062 A1 * | 9/2006 |
| WO | WO 2007/121272 A3 | 4/2007 |
| WO | WO 2008/042236 A3 | 4/2008 |

OTHER PUBLICATIONS

Salvatore et al. Loss of negative regulation by Numb over Notch is relevant to human breast carcinogenesis. J Cell Biol 167(2): 215-221, 2004.*

Parr et al. The possible correlation of Notch-1 and Notch-2 with clinical outcome and tumour clinicopathological parameters in human breast cancer. Int J Mol Med 14: 779-786, 2004.*
Reedijk et al. High-level coexpression of JAG1 and NOTCH1 is observed in human breast cancer and is associated with poor overall survival. Cancer Res 65: 8530-8537, 2005.*
Apostolopoulos et al., "Delivery of Tumor Associated Antigens to Antigen Presenting Cells Using Penetratin Induces Potent Immune Responses," *Vaccine* (2006), 3191-3202, Elsevier Ltd.
Bork, Peer, "Go Hunting in Sequence Databases but Watch Out for Traps," *Trends Genet.* (1996), 12(10):425-427, Elsevier Science Ltd.
Bork, Peer, "Powers and Pitfalls in Sequence Analysis: The 70% Hurdle," *Genome Res.* (2000), 10:398-400, Cold Spring Harbor Laboratory Press.
Brenner, Steven E., "Errors in Genome Annotation," *Trends Genet.* (1999), 15(4):132-133, Elsevier Science.
Dietz and Bähr, "Delivery of Bioactive Molecules into the Cell: The Trojan Horse Approach," *Mol. Cell. Neurosci.* (2004) 27:85-131, Elsevier Inc.
Doerks et al., "Protein Annotation: Detective Work for Function Prediction," *Trends Genet.* (1998), 14(6):248-250, Elsevier Science Ltd.
Engin et al., "Notch Signaling Contributes to the Pathogenesis of Human Osteosarcomas," *Human Mol Genet.* (2009), 18(8):1464-1470.
Farnie and Clarke, "Mammary Stem Cells and Breast Cancer—Role of Notch Signalling," *Stem Cell Rev.* (2007), 3(2):169-175.
Järver and Langel, "Cell-Penetrating Peptides—A Brief Introduction," *Biopchim. Biophys. Acta* (2006), 1758:260-263, Elsevier B.V.
Liu et al., "Inhibition of Endothelial Cell Proliferation by Notch1 Signaling is Mediated by Repressing MAPK and Pl3K/Akt Pathways and Requires MAML1," *FASEB J.* (2006), 20:1009-1011; E201-E210.
Maillard et al., "Mastermind Critically Regulates Notch-Mediated Lymphoid Cell Fate Decisions," *Blood* (2004), 104(6):1696-1702, The American Society of Hematology.
Maillard et al., "The Requirement for Notch Signaling at the β-selection Checkpoint in vivo is Absolute and Independent of the Pre-T Cell Receptor," *J. Exp. Med.* (2006), 203(10):2239-2245, The Rockefeller University Press.
Ngo et al., "Computational Complexity, Protein Structure Prediction, and the Levinthal Paradox," In K Merz, Jr. and S. Le Grand (eds), *The Protein Folding Problem and Tertiary Structure Prediction* (1994), 492-495, Birkhäuser, Boston.
Phillips, Anthony J., "The Challenge of Gene Therapy and DNA Delivery," *J. Pharm. Pharmacology* (2001), 53:1169-1174.
Pross et al., "Efficient Inhibition of Notch3 and Notch4 Family Members in vivo by a Dominant Negative Mutant of Mastermind," *Blood* (2004), 104:Abstract 1617, American Society of Hematology.

(Continued)

*Primary Examiner* — Bridget E Bunner
(74) *Attorney, Agent, or Firm* — DLA Piper LLP (US)

(57) ABSTRACT

The present invention is based on the discovery that the Notch signaling pathway is associated with cancer. Accordingly, the invention provides methods and compositions for treating cancer. Also provided are methods of modulating the expression and/or activity of proteins in the Notch signaling pathway for use in diagnoses and treatment of cancer in a subject.

5 Claims, 8 Drawing Sheets

(56) References Cited

OTHER PUBLICATIONS

Proweller et al., "Impaired Notch Signaling Promotes *De novo* Squamous Cell Carcinoma Formation," *Cancer Res.* (2006), 66(15):7438-7444, American Association for Cancer Research.

Skolnick and Fetrow, "From Genes to Protein Structure and Function: Novel Applications of Computational Approaches in the Genomic Era," *Trends Biotechnol.* (2000), 18(1):34-39, Elsevier Science Ltd.

Smith et al., "The Challenges of Genome Sequence Annotation of 'The Devil is in the Details'," *Nature Biotech.* (1997), 15:1222-1223.

Stylianou et al., "Aberrant Activation of Notch Signaling in Human Breast Cancer," *Cancer Res.* (2006), 66(3):1517-1525, American Association for Cancer Research.

Vives, Eric, "Present and Future of Cell-Penetrating Peptide Mediated Delivery Systems: 'Is the Trojan Horse Too Wild to Go Only to Troy?'," *J. Control. Release* (2005), 109:77-85, Elsevier.

Wells, James A., "Additivity of Mutational Effects in Proteins," *Biochemistry* (1990), 29(37):8509-8517, American Chemical Society.

\* cited by examiner

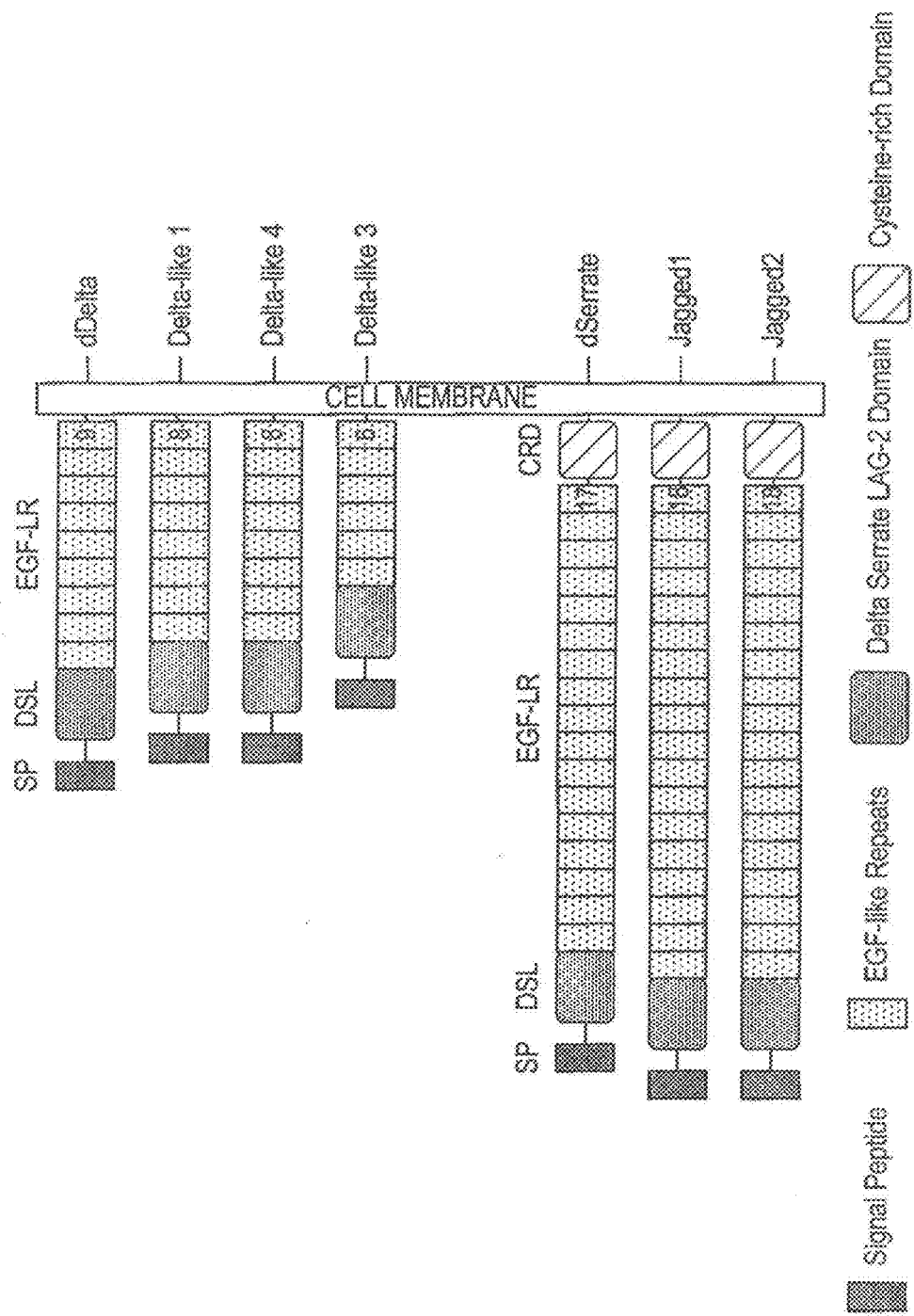

SEQUENCE LISTING

```
<160> NUMBER OF SEQ ID NOS: 9

<210> SEQ ID NO 1
<211> LENGTH: 724
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (35)..(35)
<223> OTHER INFORMATION: Xaa can be any naturally occurring amino acid

<400> SEQUENCE: 1

Met Glu Thr Asp Thr Leu Leu Leu Trp Val Leu Leu Leu Trp Val Pro
1               5                   10                  15

Gly Ser Thr Gly Asp Ala Ala Gln His His His His His His Gly Gly
            20                  25                  30

Glu Gln Xaa Leu Ile Ser Glu Glu Asp Leu Ser Arg Pro Gly Ala Arg
        35                  40                  45

Ala Val Arg Thr Lys Leu Gly Thr Glu Leu Gly Ser Arg Lys Arg Gly
    50                  55                  60

Arg Gln Thr Tyr Thr Arg Tyr Gln Thr Leu Glu Leu Glu Lys Glu Phe
65                  70                  75                  80

His Phe Asn Arg Tyr Leu Thr Arg Arg Arg Ile Glu Ile Ala His
                85                  90                  95

Ala Leu Cys Leu Thr Glu Arg Gln Ile Lys Ile Trp Phe Gln Asn Arg
            100                 105                 110

Arg Met Lys Trp Lys Lys Glu Asn Gly Ser Thr Pro Val Trp Trp Asn
        115                 120                 125

Ser Met Ala Met Asn Lys Leu Arg Gln Ser Phe Arg Arg Lys Lys Asp
    130                 135                 140

Val Tyr Val Pro Glu Ala Ser Arg Pro His Gln Trp Gln Thr Asp Glu
145                 150                 155                 160
```

```
Glu Gly Tyr Arg Thr Gly Lys Cys Ser Phe Pro Val Lys Tyr Leu Gly
            165                 170                 175
His Val Glu Val Asp Glu Ser Arg Gly Met His Ile Cys Glu Asp Ala
            180                 185                 190
Val Lys Arg Leu Lys Ala Thr Gly Lys Lys Ala Val Lys Ala Val Leu
            195                 200                 205
Trp Val Ser Ala Asp Gly Leu Arg Val Val Asp Glu Lys Thr Lys Asp
            210                 215                 220
Leu Ile Val Asp Gln Thr Ile Glu Lys Val Ser Phe Cys Ala Pro Asp
225                 230                 235                 240
Arg Asn Phe Asp Arg Ala Phe Ser Tyr Ile Cys Arg Asp Gly Thr Thr
                245                 250                 255
Arg Arg Trp Ile Cys His Cys Phe Met Ala Val Lys Asp Thr Gly Glu
                260                 265                 270
Arg Leu Ser His Ala Val Gly Cys Ala Phe Ala Ala Cys Leu Glu Arg
                275                 280                 285
Lys Gln Lys Arg Glu Lys Glu Cys Gly Val Thr Ala Thr Phe Asp Ala
            290                 295                 300
Ser Arg Thr Thr Phe Thr Arg Glu Gly Ser Phe Arg Val Thr Thr Ala
305                 310                 315                 320
Thr Glu Gln Ala Glu Arg Glu Glu Ile Met Lys Gln Leu Gln Asp Ala
                325                 330                 335
Lys Lys Ala Glu Thr Asp Lys Thr Ala Val Gly Pro Ser Val Ala Pro
                340                 345                 350
Gly Asn Thr Ala Pro Ser Pro Ser Ser Pro Thr Ser Pro Thr Pro Asp
            355                 360                 365
Gly Thr Ala Ser Ser Glu Met Asn Asn Pro His Ala Ile Pro Arg Arg
            370                 375                 380
His Ala Pro Ile Glu Gln Leu Ala Arg Gln Gly Ser Phe Arg Gly Phe
385                 390                 395                 400
Pro Ala Leu Ser Gln Lys Met Ser Pro Phe Lys Arg Gln Leu Ser Leu
                405                 410                 415
Arg Ile Asn Glu Leu Pro Ser Thr Met Gln Arg Lys Thr Asp Phe Pro
                420                 425                 430
Ile Lys Asn Thr Val Pro Glu Val Glu Gly Glu Ala Glu Ser Ile Ser
            435                 440                 445
Ser Leu Cys Ser Gln Ile Thr Ser Ala Phe Ser Thr Pro Ser Glu Asp
    450                 455                 460
Pro Phe Ser Ser Ala Pro Met Thr Lys Pro Val Thr Leu Val Ala Pro
465                 470                 475                 480
Gln Ser Pro Val Leu Gln Gly Thr Glu Trp Gln Ser Ser Gly Ala
                485                 490                 495
Ala Ser Pro Gly Leu Phe Gln Ala Gly His Arg Arg Thr Pro Ser Glu
            500                 505                 510
Ala Asp Arg Trp Leu Glu Glu Val Ser Lys Ser Val Arg Ala Gln Gln
            515                 520                 525
Pro Gln Val Ser Ala Ala Pro Leu Gln Pro Val Leu Gln Pro Pro Pro
            530                 535                 540
Pro Ala Ala Ile Ala Pro Pro Ala Pro Pro Phe Gln Gly His Ala Phe
545                 550                 555                 560
Leu Thr Ser Gln Pro Val Pro Val Gly Val Val Pro Leu Gln Pro
                565                 570                 575
Ala Phe Val Pro Thr Gln Ser Tyr Pro Val Ala Asn Gly Met Pro Tyr
```

```
                    580                 585                 590
Pro Ala Ser Asn Val Pro Val Gly Ile Thr Pro Ser Gln Met Val
            595                 600                 605
Ala Asn Val Phe Gly Thr Ala Gly His Pro Gln Thr Thr His Pro His
        610                 615                 620
Gln Ser Pro Ser Leu Ala Lys Gln Gln Thr Phe Pro Gln Tyr Glu Thr
625                 630                 635                 640
Ser Ser Ala Thr Thr Ser Pro Phe Phe Lys Pro Pro Ala Gln His Leu
                645                 650                 655
Asn Gly Ser Ala Ala Phe Asn Gly Val Asp Asn Gly Gly Leu Ala Ser
            660                 665                 670
Gly Asn Arg His Ala Glu Val Pro Pro Gly Thr Cys Pro Val Asp Pro
        675                 680                 685
Phe Glu Ala Gln Trp Ala Ala Leu Glu Ser Lys Ser Lys Gln Arg Thr
690                 695                 700
Asn Pro Ser Pro Thr Asn Pro Phe Ser Ser Asp Leu Gln Lys Thr Phe
705                 710                 715                 720
Glu Ile Glu Leu

<210> SEQ ID NO 2
<211> LENGTH: 193
<212> TYPE: PRT
<213> ORGANISM: Artificial Sequence
<220> FEATURE:
<223> OTHER INFORMATION: Synthetic construct

<400> SEQUENCE: 2

Met Glu Thr Asp Thr Leu Leu Leu Trp Val Leu Leu Leu Trp Val Pro
1               5                   10                  15
Gly Ser Thr Gly Asp Ala Ala Gln His His His His His His Gly Gly
            20                  25                  30
Glu Gln Lys Leu Ile Ser Glu Glu Asp Leu Ser Arg Pro Gly Ala Arg
        35                  40                  45
Ala Val Arg Thr Lys Leu Gly Thr Glu Leu Gly Ser Arg Lys Arg Gly
    50                  55                  60
Arg Gln Thr Tyr Thr Arg Tyr Gln Thr Leu Glu Leu Glu Lys Glu Phe
65                  70                  75                  80
His Phe Asn Arg Tyr Leu Thr Arg Arg Arg Arg Ile Glu Ile Ala His
                85                  90                  95
Ala Leu Cys Leu Thr Glu Arg Gln Ile Lys Ile Trp Phe Gln Asn Arg
            100                 105                 110
Arg Met Lys Trp Lys Lys Glu Asn Gly Ser Thr Pro Val Trp Trp Asn
        115                 120                 125
Ser Met Ala Leu Pro Arg His Ser Ala Val Met Glu Arg Leu Arg Arg
    130                 135                 140
Arg Ile Glu Leu Cys Arg Arg His His Ser Thr Cys Glu Ala Arg Tyr
145                 150                 155                 160
Glu Ala Val Ser Pro Glu Arg Leu Glu Leu Glu Arg Gln His Thr Phe
                165                 170                 175
Ala Leu His Gln Arg Cys Ile Gln Ala Lys Ala Lys Arg Ala Gly Lys
            180                 185                 190
His

<210> SEQ ID NO 3
<211> LENGTH: 593
<212> TYPE: PRT
```

<213> ORGANISM: Drosophila melanogaster

<400> SEQUENCE: 3

```
Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Tyr
            20                  25                  30

Arg Thr Gly Lys Cys Ser Phe Pro Val Lys Tyr Leu Gly His Val Glu
        35                  40                  45

Val Asp Glu Ser Arg Gly Met His Ile Cys Glu Asp Ala Val Lys Arg
    50                  55                  60

Leu Lys Ala Thr Gly Lys Lys Ala Val Lys Ala Val Leu Trp Val Ser
65                  70                  75                  80

Ala Asp Gly Leu Arg Val Val Asp Glu Lys Thr Lys Asp Leu Ile Val
                85                  90                  95

Asp Gln Thr Ile Glu Lys Val Ser Phe Cys Ala Pro Asp Arg Asn Phe
            100                 105                 110

Asp Arg Ala Phe Ser Tyr Ile Cys Arg Asp Gly Thr Thr Arg Arg Trp
        115                 120                 125

Ile Cys His Cys Phe Met Ala Val Lys Asp Thr Gly Glu Arg Leu Ser
130                 135                 140

His Ala Val Gly Cys Ala Phe Ala Ala Cys Leu Glu Arg Lys Gln Lys
145                 150                 155                 160

Arg Glu Lys Glu Cys Gly Val Thr Ala Thr Phe Asp Ala Ser Arg Thr
                165                 170                 175

Thr Phe Thr Arg Glu Gly Ser Phe Arg Val Thr Thr Ala Thr Glu Gln
            180                 185                 190

Ala Glu Arg Glu Glu Ile Met Lys Gln Leu Gln Asp Ala Lys Lys Ala
        195                 200                 205

Glu Thr Asp Lys Thr Ala Val Gly Pro Ser Val Ala Pro Gly Asn Thr
    210                 215                 220

Ala Pro Ser Pro Ser Ser Pro Thr Ser Pro Thr Pro Asp Gly Thr Ala
225                 230                 235                 240

Ser Ser Glu Met Asn Asn Pro His Ala Ile Pro Arg Arg His Ala Pro
                245                 250                 255

Ile Glu Gln Leu Ala Arg Gln Gly Ser Phe Arg Gly Phe Pro Ala Leu
            260                 265                 270

Ser Gln Lys Met Ser Pro Phe Lys Arg Gln Leu Ser Leu Arg Ile Asn
        275                 280                 285

Glu Leu Pro Ser Thr Met Gln Arg Lys Thr Asp Phe Pro Ile Lys Asn
    290                 295                 300

Thr Val Pro Glu Val Glu Gly Glu Ala Glu Ser Ile Ser Ser Leu Cys
305                 310                 315                 320

Ser Gln Ile Thr Ser Ala Phe Ser Thr Pro Ser Glu Asp Pro Phe Ser
                325                 330                 335

Ser Ala Pro Met Thr Lys Pro Val Thr Leu Val Ala Pro Gln Ser Pro
            340                 345                 350

Val Leu Gln Gly Thr Glu Trp Gly Gln Ser Ser Gly Ala Ala Ser Pro
        355                 360                 365

Gly Leu Phe Gln Ala Gly His Arg Arg Thr Pro Ser Glu Ala Asp Arg
    370                 375                 380

Trp Leu Glu Glu Val Ser Lys Ser Val Arg Ala Gln Gln Pro Gln Val
385                 390                 395                 400

Ser Ala Ala Pro Leu Gln Pro Val Leu Gln Pro Pro Pro Pro Ala Ala
```

```
                        405                 410                 415
Ile Ala Pro Pro Ala Pro Pro Phe Gln Gly His Ala Phe Leu Thr Ser
                420                 425                 430

Gln Pro Val Pro Val Gly Val Val Pro Pro Leu Gln Pro Ala Phe Val
            435                 440                 445

Pro Thr Gln Ser Tyr Pro Val Ala Asn Gly Met Pro Tyr Pro Ala Ser
        450                 455                 460

Asn Val Pro Val Val Gly Ile Thr Pro Ser Gln Met Val Ala Asn Val
465                 470                 475                 480

Phe Gly Thr Ala Gly His Pro Gln Thr Thr His Pro His Gln Ser Pro
                485                 490                 495

Ser Leu Ala Lys Gln Gln Thr Phe Pro Gln Tyr Glu Thr Ser Ser Ala
            500                 505                 510

Thr Thr Ser Pro Phe Phe Lys Pro Pro Ala Gln His Leu Asn Gly Ser
        515                 520                 525

Ala Ala Phe Asn Gly Val Asp Asn Gly Leu Ala Ser Gly Asn Arg
            530                 535                 540

His Ala Glu Val Pro Pro Gly Thr Cys Pro Val Asp Pro Phe Glu Ala
545                 550                 555                 560

Gln Trp Ala Ala Leu Glu Ser Lys Ser Lys Gln Arg Thr Asn Pro Ser
                565                 570                 575

Pro Thr Asn Pro Phe Ser Ser Asp Leu Gln Lys Thr Phe Glu Ile Glu
            580                 585                 590

Leu

<210> SEQ ID NO 4
<211> LENGTH: 60
<212> TYPE: PRT
<213> ORGANISM: Drosophila melanogaster

<400> SEQUENCE: 4

Arg Lys Arg Gly Arg Gln Thr Tyr Thr Arg Tyr Gln Thr Leu Glu Leu
1               5                   10                  15

Glu Lys Glu Phe His Phe Asn Arg Tyr Leu Thr Arg Arg Arg Arg Ile
            20                  25                  30

Glu Ile Ala His Ala Leu Cys Leu Thr Glu Arg Gln Ile Lys Ile Trp
        35                  40                  45

Phe Gln Asn Arg Arg Met Lys Trp Lys Lys Glu Asn
    50                  55                  60

<210> SEQ ID NO 5
<211> LENGTH: 62
<212> TYPE: PRT
<213> ORGANISM: Homo sapiens

<400> SEQUENCE: 5

Leu Pro Arg His Ser Ala Val Met Glu Arg Leu Arg Arg Arg Ile Glu
1               5                   10                  15

Leu Cys Arg Arg His His Ser Thr Cys Glu Ala Arg Tyr Glu Ala Val
            20                  25                  30

Ser Pro Glu Arg Leu Glu Leu Glu Arg Gln His Thr Phe Ala Leu His
        35                  40                  45

Gln Arg Cys Ile Gln Ala Lys Ala Lys Arg Ala Gly Lys His
    50                  55                  60

<210> SEQ ID NO 6
<211> LENGTH: 4
```

```
<212> TYPE: PRT
<213> ORGANISM: Artificial Sequence
<220> FEATURE:
<223> OTHER INFORMATION: Synthetic construct

<400> SEQUENCE: 6

Tyr Arg Pro Trp
1

<210> SEQ ID NO 7
<211> LENGTH: 4
<212> TYPE: PRT
<213> ORGANISM: Artificial Sequence
<220> FEATURE:
<223> OTHER INFORMATION: Synthetic construct

<400> SEQUENCE: 7

Pro Glu Ser Thr
1

<210> SEQ ID NO 8
<211> LENGTH: 2175
<212> TYPE: DNA
<213> ORGANISM: Artificial Sequence
<220> FEATURE:
<223> OTHER INFORMATION: Synthetic construct

<400> SEQUENCE: 8
atggagacag acacactcct gctatgggta ctgctgctct gggttccagg ttccactggt      60
gacgcggccc agcatcatca tcatcatcat ggcggcgaac agaaactgat ctccgaagag     120
gatctgagcc ggccaggcgc gcgcgccgta cgtacgaagc ttggtaccga gctcggatcc     180
cgcaaacgcg gaaggcagac atacacccgg taccagactc tagagctaga gaaagagttt     240
cacttcaatc gctacttgac ccgtcggcga aggatcgaga tcgcccacgc cctgtgcctc     300
acggagcgcc agataaagat tggttccag aatcggcgca tgaagtggaa gaaggagaac     360
ggatccactc cagtgtggtg gaattccatg gcgatgaaca aactacggca agcttcagg     420 agaaagaaag acgtttatgt cccagaggcc agccgtccac atcagtggca gacagatgaa     480
gaaggagtcc gcactggaaa gtgtagcttc ccagttaagt acctcggcca gtagaagtt     540 gatgagtcaa gaggaatgca catctgtgaa gatgccgtaa agagattgaa agctacggga     600
aagaaagcag tgaaggccgt tctgtgggtg tcagcggatg ggctcagagt tgtggacgag     660
aaaactaagg acctcatagt tgaccagaca atagaaaaag tttccttctg tgccccagat     720
aggaactttg acagagcctt tcttacata tgtcgcgatg caccactcg gcgatggatc     780 tgtcattgtt tcatggctgt caaagacacg ggggaaagac tgagccacgc cgtgggctgt     840
gcttttgcag cctgtttaga gcgtaaacag aagcgggaga aggagtgtgg cgtcactgct     900
acttttgatg ccagtagaac cactttcaca agagaaggat cattccgtgt cacaactgcc     960
actgagcaag ccgaaagaga ggagatcatg aaacagttgc aagatgccaa gaaagctgag    1020
acagacaaga cagctgttgg tccatcagtg gctcctggca acactgctcc atccccatcc    1080
tctcccacct ctcccactcc ggatggcact gcatcttcag agatgaacaa tcccatgct    1140 atcccacgcc ggcatgcacc aattgaacag cttgctcgtc aaggctcttt ccggggattt    1200
cctgctctta gccagaagat gtcaccctt aaacgccagc tgtccctccg catcaatgag    1260
ttgccttcca ctatgcagag gaagactgat ttcccaataa aaacacagt gcccgaggtg    1320 gaaggagagg ccgagagcat cagctccttg tgttcccaga tcaccagtgc cttcagcacg    1380
ccctctgagg acccctttctc ctccgcccca atgaccaaac cagtgacatt ggtggcacca    1440
```

```
cagtctcctg tgttacaagg gactgagtgg ggtcagtctt ctggtgctgc ctctccaggt    1500
ctcttccagg ctggtcacag acgcactccc tctgaagctg accgctggtt agaagaagtg    1560
tcaaagagtg tgcgggccca gcagcctcag gtctcagctg cccctctgca gccagttctc    1620
cagccgcctc cgcccgccgc cattgcccct ccagcacctc ctttccaagg acatgccttc    1680
ctcacgtccc agcctgtgcc cgtgggtgtg gtcccacccc tacaaccagc ctttgtccct    1740
acccagtcct accctgtggc caacgggatg ccctacccag cctctaatgt gcctgtagtg    1800
ggcatcaccc catcccagat ggtagccaat gtgtttggca ctgcaggcca ccctcagacc    1860
actcatccac atcagtcgcc aagcctggcg aagcagcaga cattccctca atatgagaca    1920
agtagtgcta ccaccagtcc cttctttaag cctcctgctc agcacctcaa tggttctgca    1980
gctttcaatg gtgtagacaa tggtgggcta gcctcaggaa acaggcatgc agaagtccct    2040
ccaggcacct gcccagtgga tcctttcgaa gctcagtggg ccgcactaga aagcaagtcc    2100
aagcagcgta caaatccttc tcctaccaac cctttctcca gtgacttaca gaaaacgttt    2160
gaaatagaac tttag                                                    2175

<210> SEQ ID NO 9
<211> LENGTH: 582
<212> TYPE: DNA
<213> ORGANISM: Artificial Sequence
<220> FEATURE:
<223> OTHER INFORMATION: Synthetic construct

<400> SEQUENCE: 9
atggagacag acacactcct gctatgggta ctgctgctct gggttccagg ttccactggt      60
gacgcggccc agcatcatca tcatcatcat ggcggcgaac agaaactgat ctccgaagag     120
gatctgagcc ggccaggcgc gcgcgccgta cgtacgaagc ttggtaccga gctcggatcc     180
cgcaaacgcg gaaggcagac atacacccgg taccagactc tagagctaga gaaagagttt     240
cacttcaatc gctacttgac ccgtcggcga aggatctaga tcgcccacgc cctgtgcctc     300
acggagcgcc agataaagat ttggttccag aatcggcgca tgaagtggaa gaaggagaac     360
ggatccactc cagtgtggtg gaattccatg gcgctgccgc ggcacagcgc ggtcatggag     420
cgccttcgcc ggcgcatcga gctgtgccgg cgccaccaca gcacctgcga ggcccgctac     480
gaggccgtgt cgcccgagcg cctggagctg gagcgccaac acaccttcgc cctgcaccag     540
cgctgcatcc aggccaaggc caagcgcgcc gggaagcact ag                        582
```

METHODS OF DETERMINING CANCER CELL RESPONSIVENESS TO A NOTCH INHIBITORY AGENT

CROSS REFERENCE TO RELATED APPLICATIONS

This application is a divisional application of U.S. application Ser. No. 12/245,518 filed Oct. 3, 2008, now issued as U.S. Pat. No. 8,119,366; which claims the benefit under 35 USC §119(e) to U.S. Application Ser. No. 61/044,215 filed Apr. 11, 2008 and to U.S. Application Ser. No. 60/978,039 filed Oct. 5, 2007. The disclosure of each of the prior applications is considered part of and is incorporated by reference in the disclosure of this application.

BACKGROUND OF THE INVENTION

1. Field of the Invention

The invention relates generally to cancer and more specifically to agents that affect the Notch pathway.

2. Background Information

Notch genes encode evolutionarily conserved, large, single pass transmembrane proteins that regulate cell fate determination. Work in *Drosophila, Caenorhabditis elegans* and mammalian cell culture has shown that Notch acts as receptors for the DSL (Delta, Serrate, Lag-2) family of ligands and signal through two downstream pathways. One of these is via the CSL (CBF1, Suppressor of Hairless, Lag-1) family of transcription factors and the other via the cytoplasmic adapter protein Deltex. In mammals, the Notch signaling pathway includes four receptors (Notch 1-4) and five ligands (Delta-like 1, 3 and 4 & Jagged 1 and 2). Mutations in these genes can result in dramatic developmental effects in humans, implicating Notch signaling in several inherited diseases (e.g., Cerebral Autosomal Dominant Arteriopathy with Subcortical Infarcts and Leukaencephalopathy (CADASIL), Alagille syndrome and spondylocostal dysostosis (SCDO)), and cancers (e.g., leukemia, skin, cervical, lung cancer, prostate, neuroblastomas, and breast cancer).

Negative regulators of Notch signaling include Numb, SEL-10 and Su(dx). In contrast, Sanpodo, Neuralized, Mind bomb, LNX, Siah1 and Mdm2, are positive regulators of the pathway. Numb is a cytoplasmic adaptor protein containing a PTB domain, which acts as a negative regulator of Notch through its interaction with the intracellular domain. Numb-Notch association promotes ubiquitination of Notch1. It has been demonstrated that Numb interacts with the cytosolic HECT domain of E3 ligase Itch and that Numb and Itch act cooperatively to promote ubiquitination of Notch1. On the other hand, Numb may inhibit Notch signaling by altering the function of Sanpodo, which is a positive regulator of the pathway. Sandopo encodes four-pass transmembrane protein, which physically interact with the full length Notch receptor on cell surface. Numb physically interacts with Sanpodo and inhibits the membrane localization of Sanpodo preventing its association with Notch. The mammalian actin-associated protein, Tropomodulin, which controls actin filament length, is a homologue of Sanpodo. Numb and Sanpodo are key regulators of the Notch pathway during developmental events.

Suppressor of Deltex (Su(dx)) is another protein originally identified in *Drosophila* that acts as a negative regulator of Notch signaling pathway. Overexpression of Su(dx) can block endogenous Notch signaling leading to ectopic vein differentiation and loss of the wing margin. In contrast, down-regulation of Su(dx) displays a wing vein gap similar to the Notch overexpression phenotype. Itch is the mouse homologue of Su(dx) and is so named because mice mutant display an itching behavior along with immunological defects. In contrast to SEL-10, Itch contains phospholipid binding motif that targets it to the plasma membrane, four WW-motifs and a HECT domain which functions as an E3 ubiquitin ligase. Itch binds to N-terminal portion of the NICD via its WW-motifs and promotes ubiquitination of NICD though its HECT domain. In mammalian cells this interaction down-regulates Notch signaling.

The first indication that the Notch signaling pathway may play a role in the neoplastic development of the mammary gland came from a common insertion site within the Notch4 gene of the Mouse Mammary Tumor Virus (MMTV) in Czech II mice. This insertion results in the expression of a truncated transcript that encodes the intracellular domain of Notch4; expression of this protein activates the signaling pathway. The causal role of Notch signaling in tumor development was shown in transgenic mice expressing this protein specifically in the mammary gland. These mice display mammary tumors within 12 months. Furthermore, cell culture experiments demonstrated that overexpression of Notch1 or Notch4 intracellular domain transforms mouse mammary epithelial cell lines leading to anchorage independent growth in soft agar.

Notch signaling is aberrantly activated in a wide range of human breast cancers. This is most clearly demonstrated by the loss of Numb and the accumulation of the Notch1 intracellular domain (NICD), which is generated by cleavage of the full length protein during signaling and transduces the Notch signal, and the upregulation of the target genes Hes1 and Hey1. Furthermore, changes in pathway components may prove to be useful prognostic markers. For example, elevated transcript levels for Notch1 and the ligand Jagged1 correlate with poor prognosis, and proteosomal degradation of Numb is seen primarily in high grade tumors. Finally, the increase in Notch signaling plays an important role in the etiology of breast cancer, as inhibiting the pathway reverts the transformed phenotype of breast cancer cell lines and prevents the growth of primary tumor cells.

Although altered Notch signaling has been linked to human diseases, including cancer, evidence for a substantial involvement of Notch in human tumors has remained elusive. Mechanistically, Numb operates as an oncosuppressor, as its ectopic expression in Numb-negative, but not in Numb-positive, tumor cells inhibits proliferation. Increased Notch signaling is observed in Numb-negative tumors, but reverts to basal levels after enforced expression of Numb. Conversely, Numb silencing increases Notch signaling in normal breast cells and in Numb-positive breast tumors. Numb/Notch biological antagonism is relevant to the homeostasis of the normal mammary parenchyma. Thus, a need exists for a method of diagnosing and treating cancer caused by aberrant signaling of the Notch pathway.

SUMMARY OF THE INVENTION

The present invention is based on the seminal discovery that some human breast cancers contain upregulation of the Notch pathway. In particular, these cancers are characterized as having increased Notch signaling and decreased expression of Numb, a negative regulator of the Notch pathway.

In one embodiment, the invention provides a method of treating cancer comprising contacting a cancer cell with a construct as shown in FIG. 3A or 3B. The method of the invention further comprises contacting the cancer cell with a chemotherapeutic agent.

In another embodiment, the invention provides a method of determining whether a cancer cell is responsive to treatment by a Notch pathway inhibitory agent comprising determining the level of Notch 1 in a cell, wherein a higher level of Notch 1 as compared with the level in a normal cell is indicative of a cell responsive to treatment by a Notch pathway inhibitory agent. Illustrative Notch pathway inhibitory agents are shown in FIG. 3A or 3B.

In one aspect, the method includes further determining the level of Numb expression in the cell, wherein a low level of Numb expression as compared with the level in a normal cell, is indicative of a cell responsive to treatment by a Notch pathway inhibitory agent or an agent that increases the expression of Numb in the cell.

The invention also provides specific constructs as illustrated in FIG. 3A and FIG. 3B.

In another embodiment, the invention provides a method of treating cancer comprising contacting a cancer cell with a construct comprising a dominant negative Mastermind isoform. In one aspect, the cancer is breast, ovarian, colon, prostate, lung, hematopoietic or pancreatic cancer for example. In a further embodiment, the cancer cell can also be contacted with a chemotherapeutic agent. In another embodiment, the cell can be contacted with Antennapedia nucleic acid or protein. (The antennapedia homeodomain is a sequence-specific transcription factor from the organism *Drosophila melanogaster*. This protein is encoded by the Antennapedia (antp) gene. Antp is a member of a regulatory system that gives cells specific positions on the anterior-posterior axis of the organism. Thus, Antp aids in the control of cell development in the mesothorax segment in *Drosophila*.) (see for example, Y.-Q. Qian et al., The Structure of the Antennapedia Homeodomain Determined by NMR Spectroscopy in Solution: Comparison With Prokaryotic Repressors, Cell 59:573 (1989)).

In another embodiment, the invention provides methods of treating cancer comprising contacting a cancer cell with a construct comprising a Numb isoform. In a further embodiment, the cancer cell can also be contacted with a chemotherapeutic agent. In another embodiment, the cell can be contacted with Antennapedia nucleic acid or protein.

In one embodiment, methods are described for determining whether a cancer cell is responsive to treatment by a Notch pathway inhibitory agent comprising determining the level of Notch 1 in a cell, wherein a higher level of Notch 1 as compared with the level in a normal cell is indicative of a cell responsive to treatment by a Notch pathway inhibitory agent. In one aspect, the Notch pathway inhibitory agent comprises a dominant negative Mastermind isoform. In another embodiment, the Notch pathway inhibitory agent comprises a Numb isoform. In yet another embodiment, the method includes determining the level of Numb expression in the cell, wherein a low level of Numb expression as compared with the level in a normal cell, is indicative of a cell responsive to treatment by a Notch pathway inhibitory agent. In a further embodiment, the cancer cell is a breast cancer cell, an ovarian cancer cell, a colon cancer cell, or a pancreatic cancer cell.

In another embodiment of the invention, methods of monitoring a therapeutic regimen for treating a subject having or at risk of having cancer, comprising determining the activity or expression of one or more genes involved in the Notch signaling pathway are described. In one aspect, the gene involved in the Notch signaling pathway is selected from the group consisting of Jagged1, Jagged2 Delta-like4, E-Cadherin, Numb, NICD Notch 3, Hey1, Hes5, or a combination thereof.

In one embodiment, methods are described for diagnosing a subject having or at risk of having cancer comprising determining the activity or expression of one or more genes involved in the Notch signaling pathway, wherein a change in activity or expression of one or more genes involved in the Notch signaling pathway as compared with the level in a normal cell is diagnostic of subject having or at risk of having cancer. In another embodiment, the gene involved in the Notch pathway is selected from the group consisting of Jagged1, Jagged2 Delta-like4, E-Cadherin, Numb, NICD Notch 3, Hey1, Hes5, or a combination thereof.

In another embodiment of the invention, method are described for identifying an agent that modulates the activity or expression of one or more genes involved in the Notch signaling pathway comprising contacting a test agent with a cell exhibiting expression of one or more genes involved in the Notch signaling pathway, and detecting a change in activity or expression of one or more genes involved in the Notch signaling pathway, thereby identifying the test agent as an agent that modulates the activity or expression of one or more genes involved in the Notch signaling pathway. In one embodiment, the gene involved in the Notch signaling pathway is selected from the group consisting of Jagged1, Jagged2 Delta-like4, E-Cadherin, Numb, NICD Notch 3, Hey1, Hes5, or a combination thereof. In another embodiment, the cell is a cancer cell. In one aspect, the cancer cell is a breast cancer cell, an ovarian cancer cell, a colon cancer cell, or a pancreatic cancer cell. In one embodiment, the agent is a chemical compound, a protein, or a nucleic acid.

In one embodiment, a method is described for delivering a compound to cells comprising contacting the cell with a compound fused to Antennapedia, or a functional portion thereof. In one aspect, the compound is a chemical, protein or nucleic acid and the Antennapedia is a nucleic acid or amino acid sequence.

BRIEF DESCRIPTION OF THE DRAWINGS

FIG. 1B depicts the transmembrane DSL ligands (Delta, Serrate, LAG 2) of the Notch receptors in *Drosophila* and mammals.

DETAILED DESCRIPTION OF THE INVENTION

The present invention is based on the discovery that the Notch signaling pathway is associated with cancer. Modulation of the expression and/or activity of proteins in the Notch signaling pathway can be used to diagnose and treat cancer in a subject.

Figure 1A:
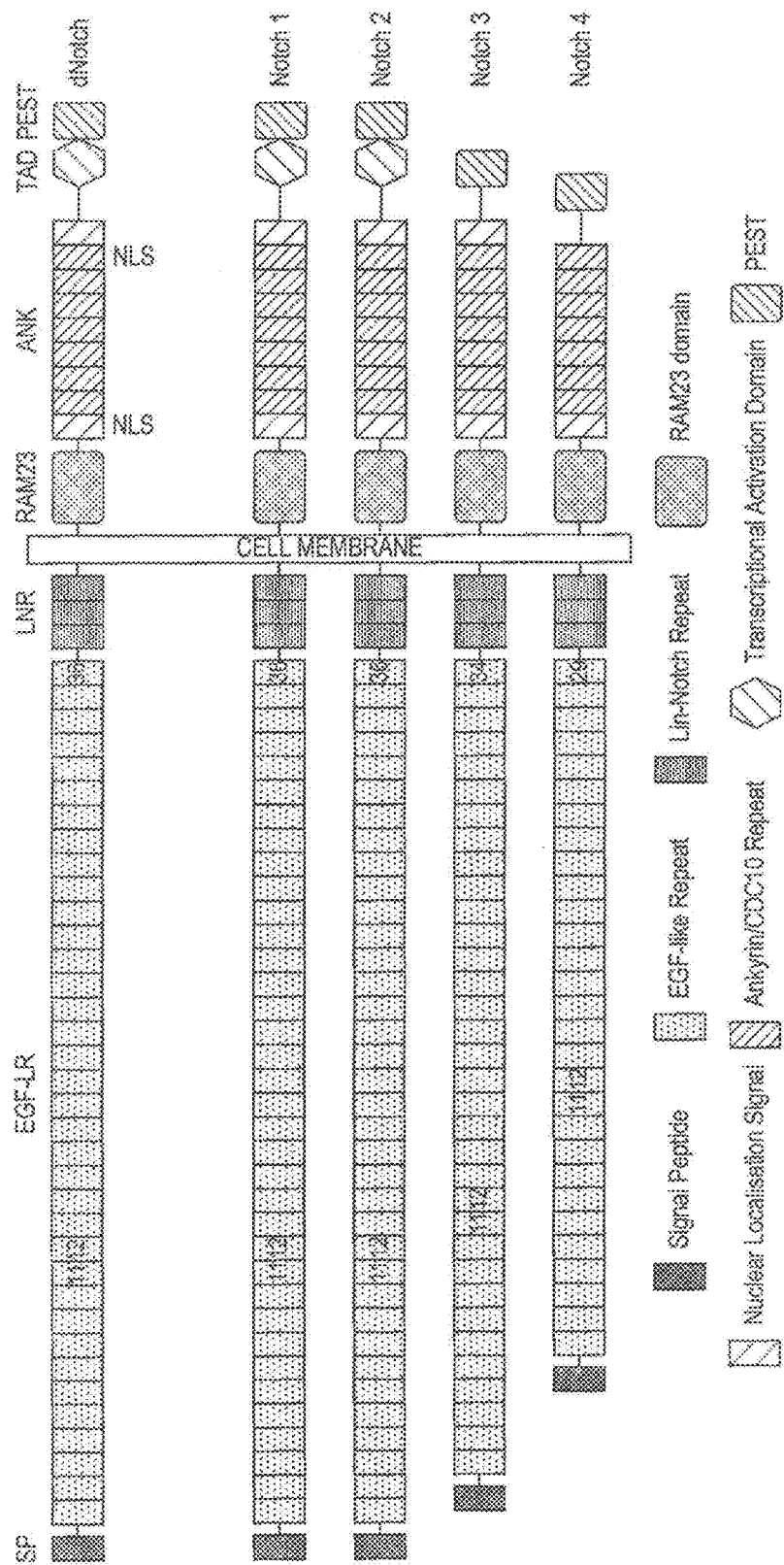
FIG. 1A is a diagrammatic representation of the *Drosophila* Notch receptor and the four known mammalian receptors.

The *Drosophila* Notch receptor is a large, single-pass transmembrane glycoprotein of 2703 amino acids (aa), which contains several distinct domains (FIG. 1A). The Notch proteins are expressed on the cell surface as heterodimers composed of a large extracellular domain non-covalently linked to the intracellular domain. The extracellular domain consists of 36 tandem Epidermal Growth Factor (EGF) like repeats (each one approximately 38 aa) and three-cysteine rich LIN12/Notch (LNR) repeats. The Notch Intracellular Domain (NICD) contains: the RAM23 domain, which binds CSL transcription factors; two nuclear localization sequences (NLS1 & 2); seven tandem CDC10/Ankyrin (ANK) repeats necessary for protein-protein interaction; the Notch cytokine response (NCR) region, transcriptional activation domain (TAD); and the PEST (SEQ ID NO.: 7) (proline (P), glutamine (E), serine (S), threonine (T)) sequence. PEST sequences are characteristic of proteins that are rapidly degraded.

There are four known mammalian Notch receptors (Notch 1-4) (FIG. 1A). Mammalian Notch1 and Notch2 contain 36 EGF-like repeats, while Notch3 and Notch4 contain 34 and 29 EGF-like repeats, respectively. All four mammalian Notch receptors contain the RAM, NLS1, ANK, and PEST domains. However, the TAD is found in Notch1 and Notch2 only, and Notch4 lacks the NLS2 and NCR motifs. The highest degree of homology between Notch receptors is within the ankyrin repeats, while the highest degree of diversity is in the C-terminal PEST sequence. Mammalian Notch1 and Notch2 proteins are cleaved (also referred as SI cleavage) within trans-Golgi apparatus (residue 1655) by a Furin-like convertase; Notch3 and Notch4 may be similarly cleaved. The long extracellular domain is bound to the transmembrane domain through a non-covalent $Ca^{2+}$-dependent interaction. This heterodimer is the predominant form of the receptor at the cell surface. It has been demonstrated that EGF-like repeats 11 and 12 are necessary for Notch DSL ligands to interact with Notch (FIG. 1A).

In *Drosophila*, Delta and Serrate are the principal ligands for the Notch receptor (FIG. 1B). Like Notch, these proteins are large single-pass transmembrane proteins with a variable number of EGF-like repeats within their extracellular domain. Delta and Serrate contain nine and seventeen EGF-like repeats respectively. They interact with Notch through a conserved cysteine-rich domain known as the DSL (Delta, Serrate, (Drosophila) Lag-2 (*C. elegans*) region at the N-terminus. In addition to these motifs, Serrate contains a third cysteine-rich (CR) domain between the EGF-like repeats and the transmembrane domain which distinguishes it from Delta. There are five Delta and Serrate homologues in mammals, Jagged1 and 2 and Delta-like1, 3 and 4 (FIG. 1B). DSL ligands have very short intracellular domains in comparison with the large intracellular domain of Notch.

Figure 1C:
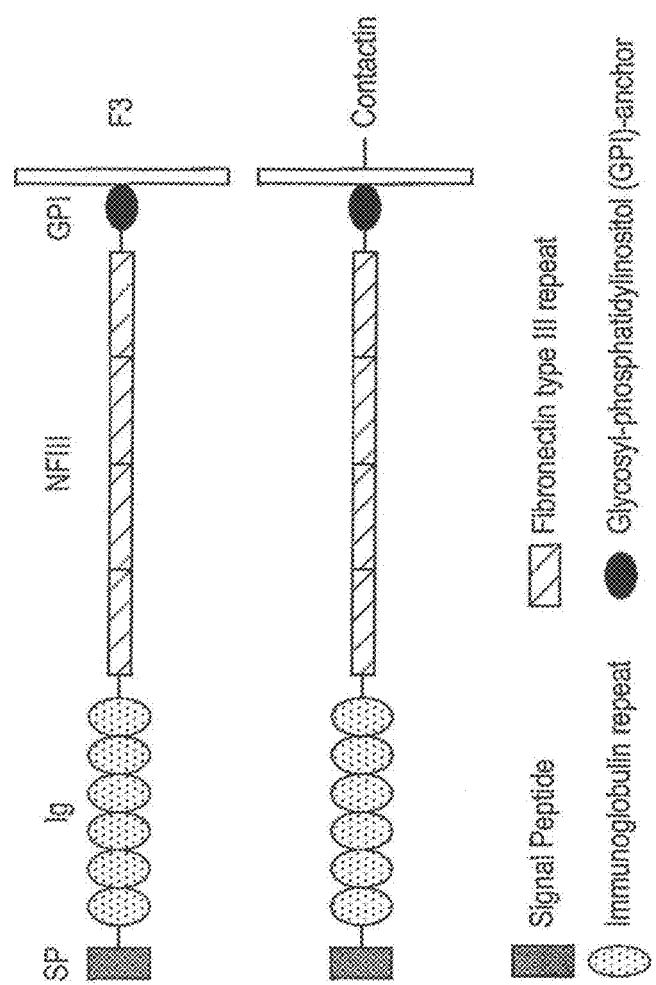
FIG. 1C is a schematic structure of mammalian F3 and Contactin ligands.

Recently, it was shown that F3/Contactin and NB-3, a member of the F3/contactin family, act as additional Notch ligands during oligodendrocyte maturation in mice (FIG. 1C). F3 is a glycosyl-phosphatidylinositol (GPI)-linked neural adhesion molecule belonging to the immunoglobulin family. F3 and Contactin belong to a group of glycoproteins containing N-terminal signal peptide, six immunoglobulin domains connected to four fibronectin type III repeats and GPI anchor domain. Contactin has an additional transmembrane and short cytoplasmic domain as compared to F3. It has been shown that F3 and NB-3 bind within EGF-like repeats 1-12 and 22-34 of the mouse Notch1 receptor.

Figure 1D:
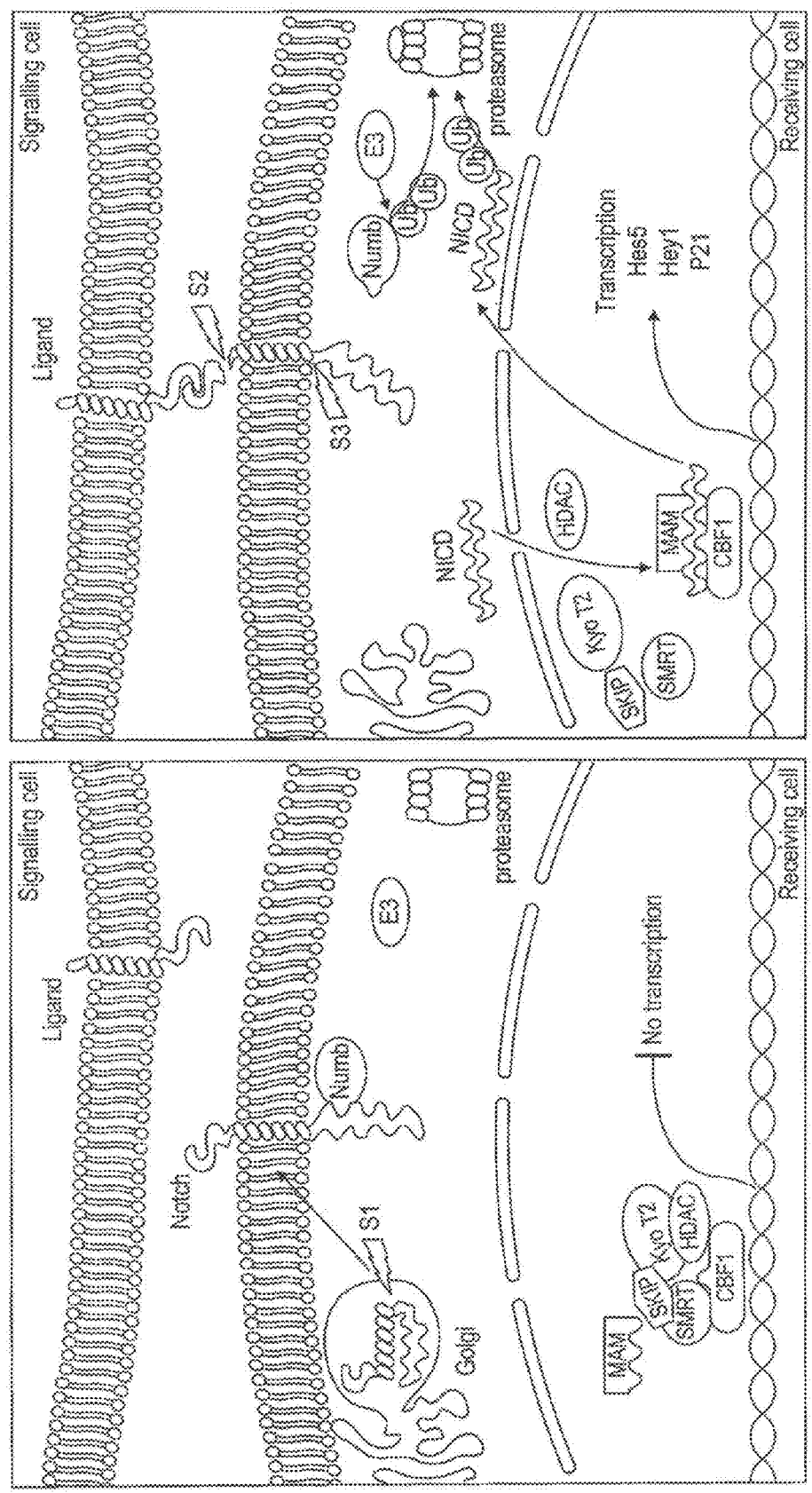
FIG. 1D is a schematic of the CBF1-dependent Notch signaling pathway.

Notch receptors are cleaved in the Golgi by the Furin convertase enzyme, (a process known as S1 cleavage), which results in the expression of a noncovalently linked heterodimer Notch receptor on cell surface (FIG. 1D). In the absence of Notch ligand interaction, Numb interacts directly with the cytoplasmic domain of Notch and inhibits its cleavage. Under these conditions CSL binds to at least four corepressors (SMRT, HDAC, SKIP and kyoT2) and suppresses transcription. Upon ligand binding, two sequential cleavages occur. One, known as S2 cleavage, mediated by the ADAM protease TACE (tumor necrosis factor α-converting enzyme) occurs at aa 1771 near the transmembrane domain and the other, cleavage known as S3 cleavage, is mediated by γ-secretase at aa 1744 within the transmembrane domain. This S3 cleavage liberates the intracellular domain of Notch (NICD), allowing its nuclear translocation and where it binds to CBF1, converting it form a transcriptional repressor to transcriptional activator by displacing the four co-repressors. Together with Mastermind (MAM), NICD and CBF1 form a larger transcriptional activator complex and recruit coactivatros such as p300. The activated CBF1 can then transcribe its target genes which include members of Hairy of enhancer of split (Hes) and Hey family. Other targets, such as p21 (target in keratinocytes) are tissue specific. The stability of Numb is regulated by E3 ligases such as Mdm2, LNX and, Shia.

In mammals, Notch signaling leads to the cleavage of NICD, which subsequently translocates to the nucleus and binds to the CBF1 (also known as RBP-Jk) transcription factor. This is the primary nuclear effector of the Notch signaling pathway and is bifunctional. In the absence of NICD, CBF1 binds to at least four co-repressors, the silencing mediator of retinoid and thyroid hormone receptor (SMRT), histone deacetylase-1 (HDAC1), KyoT2, and Ski-interacting protein (SKIP) and suppresses transcription (FIG. 1D). In contrast, the interaction CBF1 with the RAM23 and ANK repeats of the NICD displace these repressors to generate a transcriptional activator complex. The nuclear protein Mastermind-like (MAML) also interacts with this complex to further increase transcription (FIG. 1D). However, the dominant negative (DN) version of MAML1 consists of a 62-amino-acids peptide at the end terminus of MAML binds specifically to the CBF1/NICD transcriptional complex and inhibits Notch signaling activation by all four mammalian Notch receptors.

In mammals, the interaction between Notch and its DSL ligands involves EGF-like repeats 11 and 12 in the extracellular portion of Notch (FIG. 1D). Ligand/receptor interaction induces two additional proteolytic cleavages within the Notch protein that release NICD from the cell membrane; the first cleavage occurs during the maturation of Notch at S1 site. On the cell surface, proteolytic cleavage (also referred as S2 cleavage) by TNF-α Converting Enzyme (TACE) and ADAM17 metalloprotease occurs extracellularly (residue 1711) to generate a membrane tethered fragment (NEXT). This is a transient intermediate that is cleaved again (S3 cleavage) by γ-secretase (which contains presenilin and nicastrin). This occurs within the transmembrane domain (residue 1744) and leads to the release of the NICD into the cytoplasm. NICD contains two NLS domains which target it to the nucleus. In the nucleus the RAM and ANK domains NICD bind to CBF1 converting it from a transcriptional repressor to a transcriptional activator in association with MAM. The NICD/CBF1/MAM complex upregulates expression of primary target genes of Notch signaling, which include basic helix-loop-helix (bHLH) transcription factors such as hairy-and-enhancer of split 1 & 5 (Hes1 & 5) and the Hes-related transcription factors 1-3 (HRT1-3, also known as Hey1-3).

All Hes members share the C-terminal YRPW (SEQ ID NO.: 6) tetrapeptide motif which recruits the transcriptional co-repressors such as Groucho, and function as transcriptional repressors. Other targets of the pathway are tissue specific such as p21 and cardiovascular helix-loop-helix factor1 and 2 (CHF1-2) which are expressed in keratinocyte and cardiovascular development respectively. In addition to activating. Notch signaling, several proteins, including Numb, and the E3 ubiquitin ligases SEL-10 and Itch can terminate Notch signaling by promoting ubiquitination and lysosomal degradation of the Notch molecules. It has also been shown that fusions between the CBF1 and the ankyrin repeats of Notch or the transcriptional activation domain of Herpes Simplex virus (HSV) VP16, generates a constitutively active form of CBF1.

The four mammalian Notch receptors (Notch 1-4) and 5 ligands (Jagged1 and -2; Delta-like1, -3, and -4) all contain transmembrane domains such that ligand-receptor signaling occurs between adjacent cells. The ligand-receptor binding triggers a γ-secretase-dependent cleavage that releases the intracellular domain of Notch to the nucleus and facilitates an association with the transcription factor CBF-1 (also known as RBP-Jκ or CSL). The subsequent recruitment of the coactivator, mastermind-like (MAML) protein, promotes transcriptional activation of downstream effectors such as hairy and enhancer of split (HES) and the HES-related repressor protein (HERP) family of transcription factors.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein "normal cells" or "normal sample" refers to cells, or a sample from a subject, that is from the same organ and of the same type as the cells being examined. In one aspect, the corresponding normal cells comprise a sample of cells obtained from a healthy individual that does not have cancer. Such corresponding normal cells can, but need not be, from an individual that is age-matched and/or of the same sex as the individual providing the cells being examined.

As used herein, the terms "sample" and "biological sample" refer to any sample suitable for the methods provided by the present invention. The sample of cells can be any sample, including, for example, a tumor sample obtained by biopsy of a subject having the tumor, or a tumor sample obtained by surgery (e.g., a surgical procedure to remove and/or debulk the tumor). Thus, in one embodiment, the biological sample of the present invention is a tissue sample, e.g., a biopsy specimen such as samples from needle biopsy. The sample may include a blood sample, urine sample, tissue sample, or any biological fluid, for example.

The terms "cell proliferative disorder" or "cellular proliferative disorder" refer to any disorder in which the proliferative capabilities of the affected cells is different from the normal proliferative capabilities of unaffected cells. An example of a cell proliferative disorder is neoplasia. Malignant cells (i.e., cancer) develop as a result of a multistep process. The term "malignant" may refer to a tumor or hematopoietic disease no longer under normal cellular growth control.

The term "cancerous cell" as provided herein, includes a cell afflicted by any one of the cancerous conditions provided herein. The term "carcinoma" refers to a malignant new growth made up of epithelial cells tending to infiltrate surrounding tissues, and to give rise to metastases.

A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is noncancerous, e.g. its cells do not proliferate or invade surrounding tissues.

The terms "delivery" or "administration" are defined to include an act of providing a compound or pharmaceutical composition of the invention to a subject in need of treatment. The terms include enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

As used herein, the term "protein" refers to at least two covalently attached amino acids, which includes proteins, polypeptides, oligopeptides and peptides. A protein may be made up of naturally occurring amino acids and peptide bonds, or synthetic peptidomimetic structures. Thus "amino acid," or "peptide residue," as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration.

The term "fusion protein" refers to a protein that is fused to another molecule or compound. The molecule or compound can be a protein, a chemical, or a nucleic acid.

As used herein, the term "nucleic acid" means DNA, RNA, single-stranded, double-stranded or triple stranded and any chemical modifications thereof. Virtually any modification of the nucleic acid is contemplated. A "nucleic acid" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule. For methods that analyze expression of a gene, the nucleic acid isolated from a sample is typically RNA.

The present invention is based on the seminal discovery that some cancers exhibit aberrant levels of expression of genes in the Notch pathway. For example, these cancers have increased levels of Notch and decreased levels of Numb, a negative regulator of the Notch pathway.

Figure 3A:
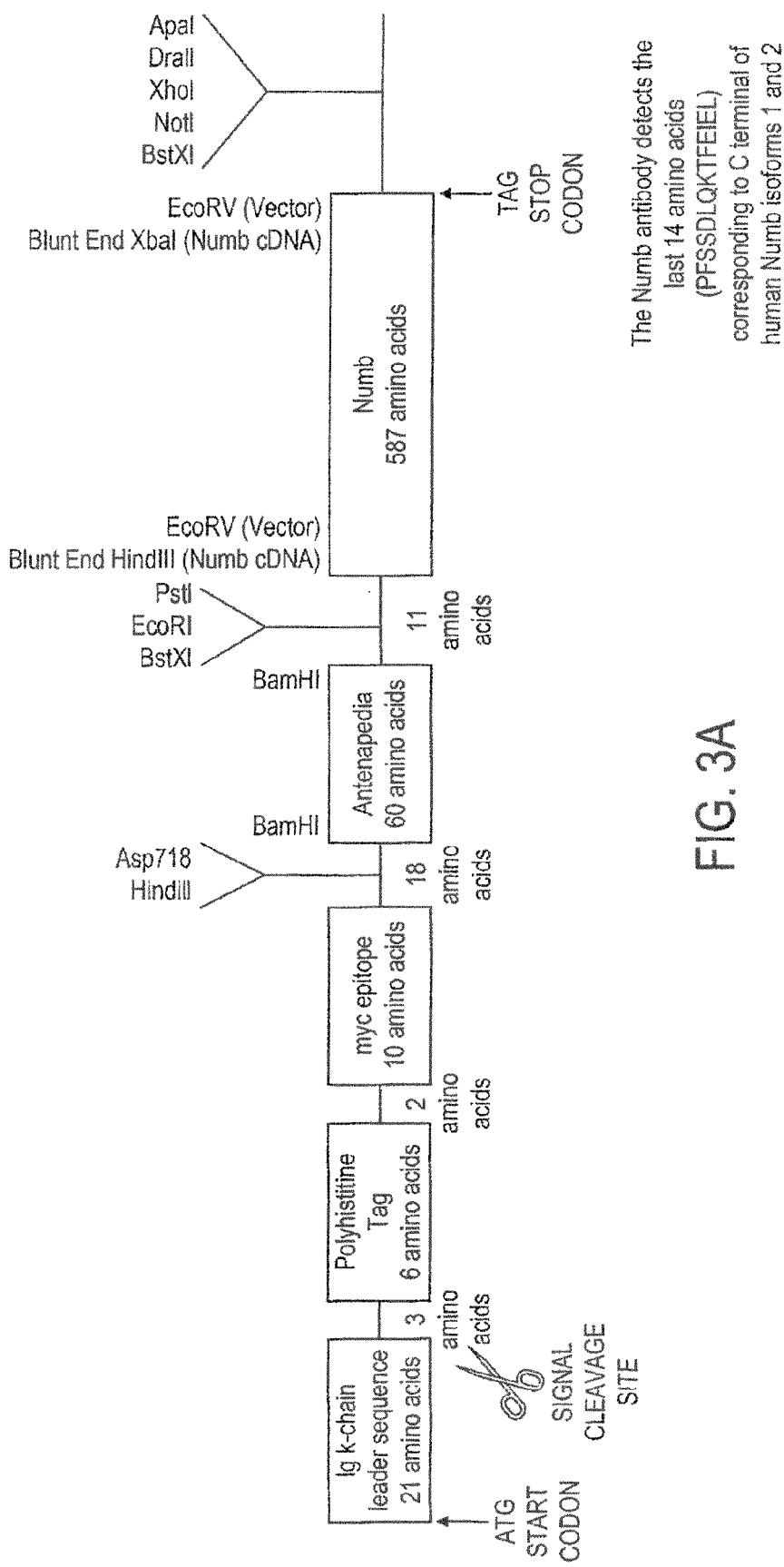
FIG. 3A illustrates the pSecTagNC/ANTP/NUMB (SEQ ID NO.: 1).
Figure 3B:
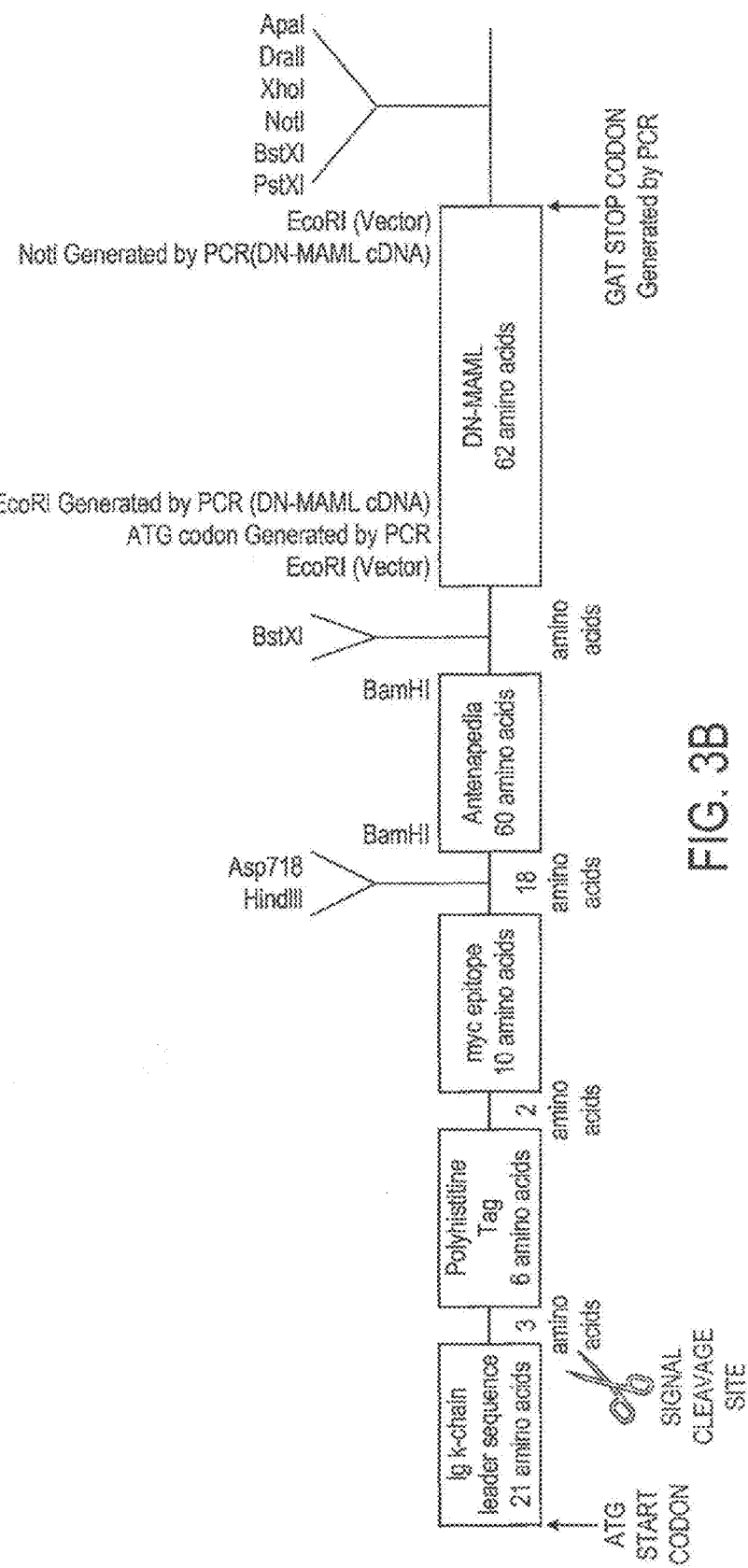
FIG. 3B illustrates the pSecTagNC/ANTP/DN-MAML (SEQ ID NO.: 2).

The present invention provides a method of treating cancer comprising contacting a cancer cell with a fusion protein, such as, for example, the construct as shown in FIG. 3A or 3B. The method of the invention further comprises contacting the cancer cell with a chemotherapeutic agent.

The agent can be administered in any way typical of an agent used to treat the particular type of cancer, or under conditions that facilitate contact of the agent with the target tumor cells and, if appropriate, entry into the cells. Entry of a polynucleotide agent into a cell, for example, can be facilitated by incorporating the polynucleotide into a viral vector that can infect the cells. If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell. Generally, an agent is formulated in a composition (e.g., a pharmaceutical composition) suitable for administration to the subject. Such formulated agents are useful as medicaments for treating a subject suffering from melanoma or non-melanoma skin cancer. Thus, the agents identified will bear a tissue-specific effect depending on the type of cancer being treated.

Candidate agents encompass numerous chemical classes, though typically they are organic molecules, and often are small organic compounds (i.e., small molecules) having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In another embodiment, the invention provides a method of determining whether a cancer cell is responsive to treatment by a Notch pathway inhibitory agent comprising determining the level of Notch 1 in a cell, wherein a higher level of Notch 1 as compared with the level in a normal cell is indicative of a cell responsive to treatment by a Notch pathway inhibitory agent. Illustrative Notch pathway inhibitory agents are shown in FIG. 3A or 3B.

The terms "inhibitor," "activator," and "modulator" are used to refer to activating, inhibitory, or modulating molecules. Inhibitors are compounds that, e.g., bind to, partially or totally block activity, decrease, prevent, delay activation, inactivate, desensitize, or down regulate the activity or expression of one or more genes in the Notch signaling pathway. "Activators" are compounds that increase, open, activate, facilitate, enhance activation, sensitize, agonize, or up regulate of one or more genes in the Notch signaling pathway. Inhibitors, activators, or modulators also include genetically modified versions of one or more genes in the Notch signaling pathway, e.g., versions with altered activity, as well as naturally occurring and synthetic ligands, substrates, antagonists, agonists, antibodies, peptides, cyclic peptides, nucleic acids, antisense molecules, ribozymes, RNAi, small chemical molecules and the like. Inhibitors can be, for example, a fusion protein as illustrated in FIGS. 3A and 3B and 4A and 4B.

In one embodiment, the methods of the invention includes further determining the level of Numb expression in the cell, wherein a low level of Numb expression as compared with the level in a normal cell, is indicative of a cell responsive to treatment by a Notch pathway inhibitory agent.

As used herein, the term "ameliorating" or "treating" means that the clinical signs and/or the symptoms associated with the cancer are lessened as a result of the actions performed. The signs or symptoms to be monitored will be characteristic of a particular cancer and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

All methods of treating cancer may further include the step of bringing the agent into association with a pharmaceutically acceptable carrier, which constitutes one or more accessory ingredients. Pharmaceutically acceptable carriers useful for formulating an agent for administration to a subject are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second (or more) compound(s) such as a diagnostic reagent, nutritional substance, toxin, or therapeutic agent, for example, a cancer chemotherapeutic agent and/or vitamin(s).

The route of administration of a composition containing the agents of the invention will depend, in part, on the chemical structure of the molecule. Polypeptides and polynucleotides, for example, are not particularly useful when administered orally because they can be degraded in the digestive tract. However, methods for chemically modifying polynucleotides and polypeptides, for example, to render them less susceptible to degradation by endogenous nucleases or proteases, respectively, or more absorbable through the alimentary tract are well known (see, for example, Blondelle et al., Trends Anal. Chem. 14:83-92, 1995; Ecker and Crook, BioTechnology, 13:351-360, 1995). For example, a peptide agent can be prepared using D-amino acids, or can contain one or more domains based on peptidomimetics, which are organic molecules that mimic the structure of peptide domain; or based on a peptoid such as a vinylogous peptoid. Where the inhibitor is a small organic molecule such as a steroidal alkaloid, it can be administered in a form that releases the active agent at the desired position in the body, or by injection into a blood vessel such that the inhibitor circulates to the target cells.

The total amount of a compound or composition to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the agent that modulates the activity or expression of one or more genes in the Notch signaling pathway to treat cancer in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

The invention provides methods of treating cancer comprising contacting a cancer cell with a construct comprising a dominant negative Mastermind isoform. The cancer cell can be, for example, a breast cancer cell, an ovarian cancer cell, a colon cancer cell, or a pancreatic cancer cell. The cancer cell can also be contacted with a chemotherapeutic agent. Additionally, the cell can be contacted with Antennapedia (ANTP).

The ANTP homeodomain is a sequence-specific transcription factor from the organism Drosophila melanogaster. This protein is encoded by the Antennapedia (antp) gene. Antp is a member of a regulatory system that gives cells specific positions on the anterior-posterior axis of the organism. Thus, Antp aids in the control of cell development in the mesothorax segment in Drosophila.

The invention also provides methods of treating cancer comprising contacting a cancer cell with a construct comprising a Numb isoform. The cancer cell can be, for example, a breast cancer cell, an ovarian cancer cell, a colon cancer cell, or a pancreatic cancer cell. The cancer cell can also be contacted with a chemotherapeutic agent. Additionally, the cell can be contacted with Antennapedia (ANTP).

In one embodiment, methods are described for determining whether a cancer cell is responsive to treatment by a Notch pathway inhibitory agent comprising determining the level of Notch 1 in a cell, wherein a higher level of Notch 1 as compared with the level in a normal cell is indicative of a cell responsive to treatment by a Notch pathway inhibitory agent. The Notch pathway inhibitory agent can be, for example, a dominant negative Mastermind isoform or a Numb isoform. In yet another embodiment, the method includes determining the level of Numb expression in the cell, wherein a low level of Numb expression as compared with the level in a normal cell, is indicative of a cell responsive to treatment by a Notch pathway inhibitory agent. The cancer cell can be, for example, a breast cancer cell, an ovarian cancer cell, a colon cancer cell, or a pancreatic cancer cell.

In another embodiment of the invention, methods of monitoring a therapeutic regimen for treating a subject having or at risk of having cancer, comprising determining the activity or expression of one or more genes involved in the Notch signaling pathway are described. The gene involved in the Notch signaling pathway can be, for example, Jagged1, Jagged2 Delta-like4, E-Cadherin, Numb, NICD Notch 3, Hey1, or Hes5.

In one embodiment, methods are described for diagnosing a subject having or at risk of having cancer comprising determining the activity or expression of one or more genes involved in the Notch signaling pathway, wherein a change in activity or expression of one or more genes involved in the Notch signaling pathway as compared with the level in a normal cell is diagnostic of subject having or at risk of having cancer. The gene involved in the Notch signaling pathway can be, for example, Jagged1, Jagged2 Delta-like4, E-Cadherin, Numb, NICD Notch 3, Hey1, or Hes5.

In another embodiment of the invention, method are described for identifying an agent that modulates the activity or expression of one or more genes involved in the Notch signaling pathway comprising contacting a test agent with a cell exhibiting expression of one or more genes involved in the Notch signaling pathway, and detecting a change in activity or expression of one or more genes involved in the Notch signaling pathway, thereby identifying the test agent as an agent that modulates the activity or expression of one or more genes involved in the Notch signaling pathway. The gene involved in the Notch pathway can be, for example, Jagged1, Jagged2 Delta-like4, E-Cadherin, Numb, NICD Notch 3, Hey1, or Hes5. The cell can be a cancer cell, and can be, for example, a breast cancer cell, an ovarian cancer cell, a colon cancer cell, or a pancreatic cancer cell. The agent can be, for example, a chemical compound, a protein, or a nucleic acid.

The invention includes methods for delivering a compound to cells comprising contacting the cell with a compound fused to Antennapedia, or a functional portion thereof. The compound can be, for example, a chemical, protein or nucleic acid.

The methods of the invention can be performed by contacting samples of cells ex vivo, for example, in a culture medium or on a solid support. Alternatively, or in addition, the methods can be performed in vivo, for example, by transplanting a cancer cell sample into a test animal (e.g., a nude mouse), and administering the test agent or composition to the test animal. An advantage of the in vivo assay is that the effectiveness of a test agent can be evaluated in a living animal, thus more closely mimicking the clinical situation. Since in vivo assays generally are more expensive, they can be particularly useful as a secondary screen, following the identification of "lead" agents using an in vitro method.

When performed in a high throughput (or ultra-high throughput) format, the methods of the invention can be performed on a solid support (e.g., a microtiter plate, a silicon wafer, or a glass slide), wherein cell samples and/or genes of interest are positioned such that each is delineated from each other (e.g., in wells). Any number of samples (e.g., 96, 1024, 10,000, 100,000, or more) can be examined in parallel using such a method, depending on the particular support used. Where samples are positioned in an array (i.e., a defined pattern), each sample in the array can be defined by its position (e.g., using an x-y axis), thus providing an "address" for each sample. An advantage of using an addressable array format is that the method can be automated, in whole or in part, such that cell samples, reagents, genes of interest, and the like, can be dispensed to (or removed from) specified positions at desired times, and samples (or aliquots) can be monitored, for example, for activity or expression of one or more genes associated with the Notch signaling pathway.

Examples of chemotherapeutic agents that can be used in combination with agents described herein include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs may also be used in combination with the agents described herein, including but not limited to nonsteroidal anti-inflammatory drugs and corticosteroids, and antiviral drugs, including but not limited to ribivirin, vidarabine, acyclovir and ganciclovir, may also be combined in compositions and methods of the invention. Two or more combined compounds may be used together or sequentially.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLES

Example 1

Detection of Notch Components in Normal and Breast Cancer Human Samples

Experiments were performed in order to elucidate the nature of Notch signaling in human breast cancer. Two normal (A and B) and twenty breast cancer samples (Group C, D, E, F, G) were obtained for Notch expression analysis (Table 2.1). All samples were accompanied by pathology reports. Breast cancer samples were categorized into five groups (Table 1, group C, D, E, F, G) based on the expression of ER, PR, erbB2, EGFR in the tumors, which correlates with prognosis and clinical outcome. In addition, within each group the tumors were of various types (lobular or ductal) and grades (I, II, III). The cells of grade I tumors are usually well-differentiated and most of the times have normal structures and functions. A grade II breast tumor has cells that are starting to look abnormal. On the other hand, the cells of grade III breast tumor are usually poorly differentiated or undifferentiated, have no specialized structure, and tend to grow and spread more aggressively. Breast cancer patients with ER/PR positive tumors have the best prognosis and clinical outcome of all other breast cancer types. 70% of ER/PR positive tumors respond to hormonal therapy whilst less than 10% of ER/PR negative and approximately 40% of the ER-positive/PR-negative breast tumors respond. ErbB2-positive tumors are typically aggressive cancers with unfavorable clinical outcome. Patients with erbB2-positive tumors showed only 40% survival at 5 years compared with more than 80% of patients with erbB2-negative tumors. ER-negative, erbB2-positive patients have very poor prognosis and there are fewer treatment strategies for this tumor type than any other breast cancer tumor type. It has been suggested that erbB2/ER positive tumors have better response to hormonal therapy than erbB2-positive ER-negative tumors. Out of the 20 samples 13 were ductal carcinoma and 7 were lobular carcinoma. Out of 13 ductal carcinomas samples one was grade I, four were grade II, six were grade III and one was ductal carcinoma in situ (DCIS). The grade was unknown for any of the lobular carcinoma samples. The twenty two samples (two normal, twenty tumorigenic) were weighed and divided in half for Western blotting and immunohistological analysis.

| | | Normal Breast Samples |
|---|---|---|
| A | ADB57 | Sample obtained during reduction mastectomy |
| B | ADB56 | Sample obtained during reduction mastectomy |

TABLE 2.1

Breast tissue samples.
Breast Cancer Samples*

| | Groups | Lab No | % ER | % PR | erbB2 | EGFR | Type | Grade |
|---|---|---|---|---|---|---|---|---|
| ER+ PR+ | C1 | 2882 | 91 | 77 | – | N/A | Ductal | I |
| erbB2– | C2 | 3512 | 99 | 93 | – | N/A | Ductal | II |
| | C3 | 2963 | 96 | 96 | – | N/A | Ductal | II |
| | C4 | 2082 | 73 | 90 | – | N/A | Ductal | III |
| | C5 | 2150 | 89 | 95 | – | N/A | Lobular | |
| | C5 | 2088 | 95 | 95 | – | N/A | Lobular | |
| | C7 | 2130 | 97 | 41 | – | N/A | Lobular | |
| ER+ PR– | D1 | 2220 | 46 | 0 | – | N/A | Ductal | II |
| erbB2– | D2 | 2162 | 90 | 15 | – | N/A | Ductal | II |
| | D3 | 2209 | 89 | 4 | – | N/A | Ductal | III |
| | D4 | 2143 | 95 | 2 | – | N/A | Ductal | III |
| | D5 | 2099 | 89 | 0 | – | N/A | Lobular | |
| | D6 | 1891 | 57 | 0 | – | N/A | Lobular | |
| | D7 | 1933 | 65 | 0 | – | N/A | Lobular | |
| ER+ | E1 | 1849 | 80 | 70 | 3+ | N/A | Ductal | II |
| erbB2+ | E2 | 1156 | 80 | 1 | 2+ | N/A | Lobular | DCIS |
| | E3 | 1223 | 90 | 15 | 3+ | N/A | Ductal | |
| ER– erbB2+ | F1 | 1952 | 0 | 0 | 3+ | N/A | Ductal | III |

TABLE 2.1-continued

Breast tissue samples.
Breast Cancer Samples*

| | Groups | Lab No | % ER | % PR | erbB2 | EGFR | Type | Grade |
|---|---|---|---|---|---|---|---|---|
| ER– | G1 | 3077 | 0 | 0 | N/A | 2/3 | Ductal | III |
| EGFR+ | G2 | 3227 | 0 | 0 | N/A | 2/3 | Ductal | III |

*0%: No ER or PR expression, 50%: moderate ER or PR expression, 100%: strong ER or PR expression, 2+: moderate erbB2 expression, 3+: strong erbB2 expression, 2/3: moderate EGFR expression.
Lobular: lesion found in the lobules,
Ductal: lesion found within the ducts,
DCIS: Ductal carcinoma in situ.
Grade I, Grade II and Grade III indicate low, moderate and high degree of nuclear differentiation respectively.
N/A: Not available,
–: negative.

In addition, three normal (MCF-10A, MTSV1-7 HB4A) and eight tumorigenic (Hs578T, MDA-MB468, MCF7, ZR75T, CAL51, MDA-MB231, SK-BR3, and PMC42) human mammary epithelial cell lines were available for Western blotting analysis. Table 2.2 indicates the expression of ER, PR, ErbB2, and EGFR expression in three normal MCF-10A, MTSV1-7, HB4A and nine tumor Hs578T, MDA-MB468, MCF7, ZR75T, CAL51, MBA-MB231, SK BR3, PMC42 human breast epithelial cell lines.

TABLE 2.2

Mammary epithelial cell lines.

| | ER | PR | erbB2 | EGFR | Malignancy | Tumor-igenic |
|---|---|---|---|---|---|---|
| MCF-10A | – | – | – | – | Normal | No |
| MTSV1-7 | – | – | – | – | Normal | No |
| HB4A | – | – | – | – | Normal | No |
| Hs578T | – | – | – | + | Ductal Carcinoma | No |
| MDA MB468 | – | – | – | + | Adenocarcinoma | Yes |
| MCF7 | + | + | – | – | Adenocarcinoma | Yes |
| ZR75T | + | – | + | + | Ductal carcinoma | Yes |
| CAL51 | – | N/A | N/A | N/A | Ductal carcinoma | Yes |
| MDA MB231 | – | – | + | – | Adenocarcinoma | Yes |
| SK BR3 | – | – | + | + | Adenocarcinoma | Yes |
| PMC42 | + | + | N/A | N/A | Carcinoma | Yes |

ER: oestrogen receptor,
PR: progesterone receptor,
EGFR: epidermal growth factor receptor,
+: positive,
–: negative,
N/A: Not available To determine whether Notch signaling is altered within breast tumors the expression of the Notch receptors and ligands detected in normal tissue was analyzed in two normal and twenty breast cancer tissue samples by Western blot analysis. In addition, NICD protein levels and the expression of Numb were examined. Numb is a cytoplasmic adaptor protein that interacts with the intracellular domain of Notch. It acts as a negative regulator of the pathway as it is required for ubiquitination and downregulation of NICD activity.

Jagged2 was downregulated in five out of the seven tumor samples in the ER+/PR+/erbB2– category, two out of seven in the ER+/PR–/erbB2– category, two out of the three in the ER+/erbB2+ samples and remained unchanged in the ER–/erbB2+ and ER–/EGFR+ samples when compared to normal tissue. The expression of Numb was abolished in all breast cancer samples. In contrast, expression of NICD was upregulated in all breast cancer samples when compared to two normal samples. In addition, truncated, lower molecular weight NICD was observed in several breast cancer samples, suggesting that the Notch receptors may be mutated in breast cancer.

Jagged2 downregulation was determined by Western analysis of proteins extracted from ER+/ER+/erbB2– (C1-C7) breast cancer samples, normal breast tissue samples (A and B), four ductal carcinomas, and three lobular carcinomas. Samples were separated by SDS-PAGE and probed with Numb, Cleaved Notch1 (NICD), Notch1, Jagged2, Delta-like4 and E-Cadherin primary antibodies. Numb was downregulated in all seven cancer samples compared with the two normal samples. In contrast, the activated form of Notch was upregulated in all seven breast cancer samples. Jagged2 was downregulated in three out of four ductal (C1, C3, and C4) and in two out of three lobular (C5 and C6) breast cancer samples. Delta-like4 was downregulated in two of four ductal and from all three lobular breast tumor samples. E-Cadherin was down regulated in all the tumor samples. In sample number C2, an additional lower molecular weight form of cleaved Notch was present. In samples C2, C4, C6, and C7 an additional lower molecular weight form of Jagged2 was present.

Additionally, Western analysis of proteins extracted from ER+/PR–/erbB2– (D1-D7) breast cancer samples was performed. Total lysates were isolated from two normal (A and B), four ductal, and three lobular ER+/PR–/erbB2– breast tumor samples and the proteins were separated by SDS-PAGE and probed with Numb, Cleaved Notch (NICD), Notch1, Jagged2, Delta-like4 and E-cadherin primary antibodies. Numb was downregulated in all seven cancer samples compared with the two normal ones. In contrast, the activated form of Notch was upregulated in all seven samples. Jagged2 was down regulated in three out of four ductal and in all three lobular samples. Delta-like4 was downregulated in three out of four ductal and in all three lobular tumor samples. E-Cadherin was downregulated in two out of four ductal and in all lobular breast cancer samples. In sample numbers D1 and D3 additional lower molecular weight forms of Jagged2 were present. The epithelial marker Desmoplakin served to normalize for the epithelial cells within each sample.

Western analysis was also performed on proteins extracted from ER+/erbB2+ (E1-E3), ER–/erbB2+ (F1), ER–/EGFR+ (G1 and G2) breast cancer samples. Total cell lysates were extracted from two normal (A and B), three ER+/erbB2+, one ER–/erbB2+ and two ER–/EGFR+ breast tumor samples lysates were separated by SDS-PAGE and probed with Numb, Cleaved Notch (NICD), Jagged2, Delta-like4 and E-Cadherin primary antibodies. Numb was downregulated in all seven cancer samples compared with the two normal ones whilst the activated form of Notch was upregulated in all seven. Jagged2 was downregulated in two out of three ER+/ erbB2+ cancer samples. Delta-like4 was downregulated in all ER+/erbB2+ samples. E-Cadherin was downregulated in four out of seven samples. An additional lower molecular weight forms of cleaved NICD and Jagged2 were present in several samples. The epithelial marker Desmoplakin served to normalize for the epithelial cells within each sample.

A truncated lower molecular weight Jagged2 was been observed in several breast cancer samples. However, the relevance of this isoform is not clear. The expression of Delta-like4 varies in normal and breast cancer samples, but overall it is downregulated in breast tumor samples when compared to normal samples. E-Cadherin was downregulated in several tumors.

Since Western analysis does not distinguish between epithelial and stromal tissue, immunohistochemistry on the above mammary tissue samples, was performed to establish the localization of Notch1 overexpression within the tumors. Intense Notch1 (NICD) staining within the epithelial cells as judged by mammary epithelial marker Muc1 was accompanied by downregulation of Numb. In addition, intense Notch3 staining was detected within the epithelial cells. Jagged1 and Jagged2 expression was limited to the epithelial cells. These data demonstrate that the Notch pathway is upregulated during breast cancer development and progression.

Example 2

Detection of Notch Components in Normal and Breast Cancer Cell Lines

To support the Western blot and immunohistochemistry results from the breast cancer samples, Western blot analysis on three normal (MCF-10A, MTSV1-7 HB4A) and eight tumorigenic (Hs578T, MDA-MB468, MCF7, ZR75T, CAL51, MDA-MB231, SK-BR3 and PMC42) human breast epithelial cell lines was performed. The results were consistent with those obtained from tissue samples.

Western blots were probed with Numb, cleaved Notch (NICD), Notch1, Notch 3, Jagged1, Jagged2, Delta-like4, E-Cadherin, Hey1 and Hes5 primary antibodies. Numb was downregulated in all nine cancer cell lines compared with the three normal lines. In contrast, the activated form of Notch was upregulated in all nine lines. Truncated forms of the activated forms on Notch were observed in five of the tumor cell lines. In addition, Hey2 and Hes5 expression was upregulated in all breast cancer cells demonstrating that the accumulation of NICD correlates with an increase in Notch signaling. Notch3 was upregulated in six out of nine (Hs578T, MDA MB468, MCF7, ZR75T, CAL51, SK BR3) and Jagged1 was upregulated in seven out of nine (Hs578T, MDA MB468, ZR75T, MDA MB231, SK BR3, MDA MB435, PMC42) of the cell lines. Together these results indicate that Notch signaling is activated in all the breast cancer cell lines analyzed. In contrast, Jagged2 was downregulated in seven out of nine tumor cell lines tested and higher molecular weight forms of Jagged2 were detected in several tumor cell lines. Delta-like4 was downregulated in three (Hs578T, ZR75T, SK BR3) out of nine tumor cell lines. E-Cadherin was downregulated in five (Hs578T, ZR75T, MDA MB231, SK BR3, PMC42) out of nine tumor cell lines.

The results in this analysis strongly indicate that Notch signaling is increased during breast cancer progression. Components of the Notch signaling pathway were overexpressed in all breast cancer tissue samples and cells lines tested. Furthermore, expression of the negative regulator, Numb, was consistently downregulated in all the samples analyzed. However, more importantly the NICD accumulation seen is a direct biochemical indication of Notch signaling. Consistent with this, expression of the target genes Hes5 and Hey1 were upregulated in the breast cancer cell lines.

Accumulation of truncated NICD molecules has also been observed in several breast cancer samples and in mammary epithelial cell lines. Similar truncated forms have been detected in T-cell acute lymphoblastic leukemia and have been shown to be due to mutations, which generate frameshifts or premature stop codons within the PEST sequence of Notch1. The resultant Notch1 proteins are more stable as the PEST domain contains sequences important for NICD degradation. Consequently, these mutations lead to increase Notch signaling. The presence of truncated Notch1 (NICD) molecules in the human breast cancer samples analyzed here suggest that similar activating mutations may occur in breast cancer.

Finally, analysis of Notch expression in relation to the prognostic markers (PR, ER, erbB2, EGFR) revealed no significant correlation in either the breast cancer specimens or cell lines. The results of this analysis provide strong evidence that the Notch pathway is altered in human breast cancer.

Example 3

Inhibiting Notch Signaling Reverts the Transformed Phenotype of the Human Breast Cancer Cell Lines MDA-B231 and MCF7

The results from breast cancer patients and cell lines analysis show that Notch signaling was activated in all twenty human breast cancer samples and eight tumorigenic mammary epithelial cell lines analyzed. To determine if the increase in Notch signaling is involved in tumor development, Notch signaling was inhibited in two different breast cancer cell lines by overexpressing Numb. The two cell lines chosen for this experiment were MDA-MB-231 and MCF7. The MDA-MB231 cell line is derived from an adenocarcinoma that does not express ER, PR, EGFR, and E-Cadherin but strongly expresses erbB2 (see Table 2). It is also reported to be highly metastatic when injected into nude mice. In contrast, the MCF7 cell line is ER, PR, E-Cadherin positive and erbB2, EGFR negative (see Table 2.1) and is also derived from adenocarcinoma, but does not metastasize when injected into nude mice.

To investigate the potential role of Numb in cellular transformation, MCF7 and MDA-MB231 cell lines stably expressing Numb were generated. The two cell lines were transfected with a pcDNA3.1 expression vector encoding the Numb protein and carrying the neomycin resistance cassette. Cells carrying stable integrations of the vector were selected with geneticin. MCF7 and MDA-MB231 cell lines carrying the empty pcDNA3.1 vector were also generated as controls. As judged by Western blotting, Numb expression levels were increased in the MCF7/Numb and MDA-MB231/Numb cell lines compared to the parental and vector control cells. Overexpression of Numb was accompanied by the downregulation of NICD and Hey1. Upregulation of E-Cadherin was also observed in MCF7/Numb cells, but not in MDA-MB231/Numb cells.

Figure 2A:
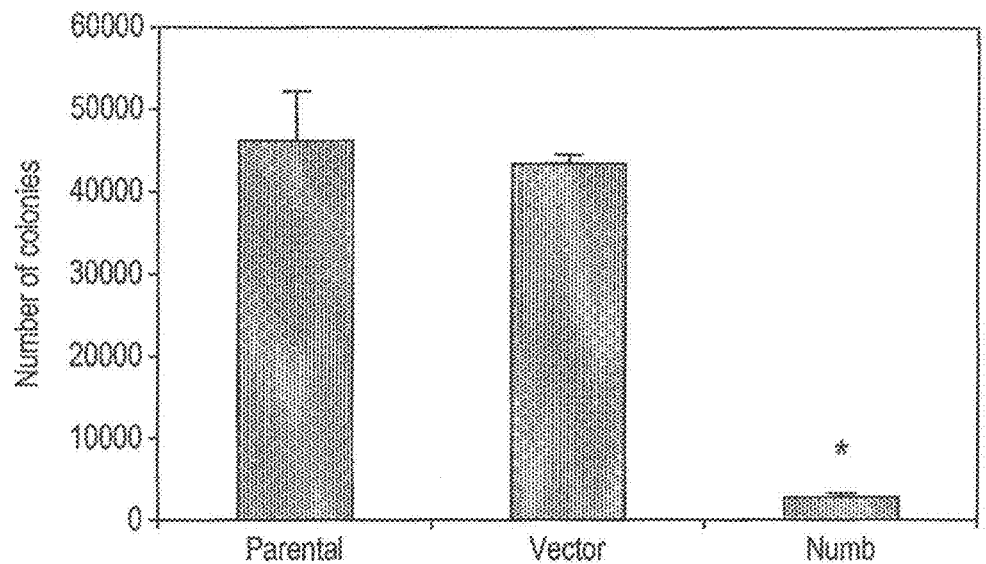
FIG. 2A is a graph depicting the number of colonies formed in soft agar from MCF7 cells from the parental, vector control and MCF7/Numb transfected cells.
Figure 2B:
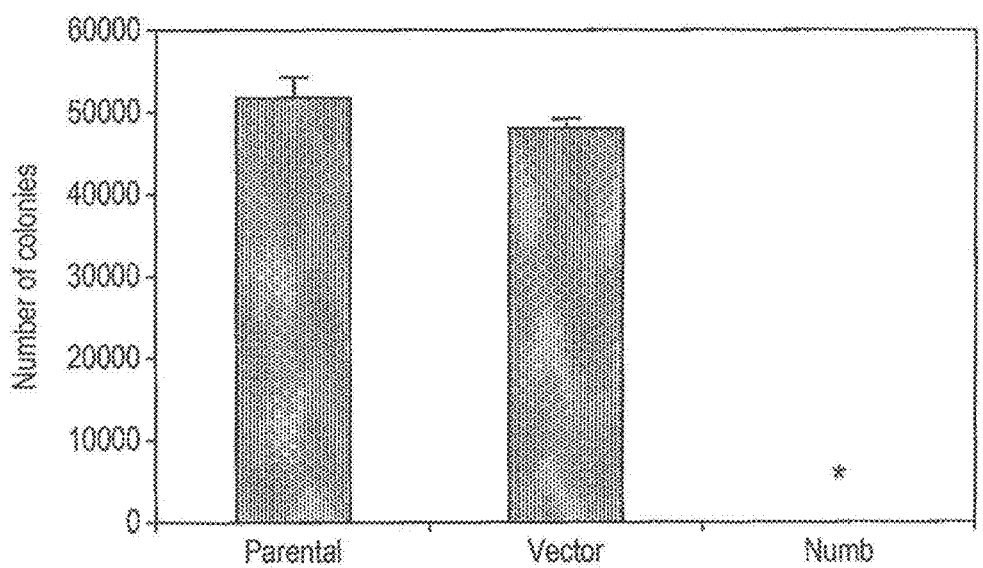
FIG. 2B is a graph depicting the number of colonies formed in soft agar from MCF7 cells from the parental, vector control and MDA-MB231/Numb transfected cells.

To assess the effect of Numb on cell morphology, parental, vector control and MCF7/Numb or MDA-MB231/Numb cells were analyzed. Parental and vector control MCF7 cells exhibited a tumorigenic, spindle-like phenotype. In contrast, the phenotype of MCF7/Numb cells changed to a normal epithelial cobblestone-like morphology. In addition, MCF7/Numb cells grew in organized islands of cell in close contact to each other compared to the disorganized growth of the parental and vector control cell lines. In contrast, MCF7/Numb cells displayed a cobblestone epithelial morphology which resembles a normal cell line. This change in morphology suggests that the MCF7/Numb cell line has lost its transformed phenotype. However, to test this more rigorously and to test the MDA-MB231/Numb cell line, the two cell lines were plated in soft agar. The number of colonies formed by MCF7/Numb and MDA-MB231/Numb cells fell to 5% and 0%, respectively, compared to the number of those formed by parental and vector control cells (FIGS. 2A and 2B). The result strongly suggests that Notch signaling is required to maintain the transformed phenotypes in MCF7 and MDA-MB231 cells.

The data suggests that the activation of Notch signaling is an important event for the transformation of mammary epithelial cells. In MCF7 cells, inactivation of the Notch pathway by Numb upregulates E-Cadherin expression and restores a normal epithelial cell morphology. This morphological change is probably due to the restoration of adherens junctions. The ability to form colonies of MCF7/Numb and MDA-MB231/Numb cells in soft agar was decreased, suggesting that the anchorage-independent proliferation of both cell lines was blocked by Numb.

Additionally, attenuation of notch signaling pathway using Numb inhibits tumor formation in immunodeficient nude mice. $5\times10^5$ cells stably expressing Numb or the empty vector were injected into the right or left flank of immunodeficient nude mice respectively. Tumor growth was supported only in left flank injected with cells expressing the empty vector and not in right flank injected with cell expressing the Notch inhibitor Numb.

Example 4

TR3 and TR4 Products Against Notch Activation

Low biomembrane permeability has conventionally posed an obstacle to the delivery of anticancer polypeptide moieties and has limited their therapeutic value. The demonstration that translocation of peptides across biological membranes can occur not through the classical endocytosis pathway, but through a seemingly energy-free mechanism has unveiled novel possibilities in biomedical research.

The methods of the invention utilize the cell-translocating abilities of the Trojan peptide Antenapedia (ANTP) to treat cancer. "Trojan horse" peptides are small proteins or regions of proteins, otherwise called protein transduction domains (PTDs), which have the ability to traverse biological membranes efficiently including the blood-brain barrier in a temperature-, receptor- and transporter-independent fashion. Their tremendous therapeutic potential lies in the fact that the peptides can carry along any pharmaceutical compound (chemicals, proteins, DNA) that is fused onto them, irrespective of its physical properties. One such peptide is the *Drosophila* homeotic transcription factor ANTP. The ANTP homeodomain is a sequence-specific transcription factor from the organism *Drosophila melanogaster*. This protein is encoded by the Antennapedia (antp) gene. Antp is a member of a regulatory system that gives cells specific positions on the anterior-posterior axis of the organism. Thus, Antp aids in the control of cell development in the mesothorax segment in *Drosophila*.

The homeobox domain, or homeodomain, is one that binds DNA through a helix-turn-helix structural motif. Proteins that contain a homeobox domain usually play a role in development, and many of these are sequence-specific transcription factors. The ANTP homeodomain is 60 amino acid residues long and contains four alpha helices. This motif is similar to those found in prokaryotic repressor proteins.

A fusion protein was genetically engineered, consisting of Antennapedia-Numb (Tr3 product), and was tested for its ability to target tumor cells in vivo (FIG. 3A). The sequence of the Tr3 fusion protein is listed in SEQ ID NO.:1. The Numb sequence alone is listed in SEQ ID NO.: 3.

Example 5

Laboratory Production and Characteristics of ANTP/DN-MAML

Mastermind-like (MAML) is a glutamine-rich nuclear protein essential for Notch signaling activation. MAML is a co-activator for all four Notch receptors. Mastermind complexes with the intracellular portion of activated Notch (NICD), the transcription factor CBF1 and DNA. This results in the activation of the Notch target genes Hes and Hey which comprise a family of transcriptional repressors. However, a truncated version of MAML that can maintain an association with the complex, behaves in a dominant negative (DN) fashion and inhibits Notch activation. DN-MAML consists of a 62-amino-acid kinked α-helix that forms a stable ternary complex through contacts on both CBF1 and the ankyrin repeats of Notch1 but which lacks the C-terminal portions of MAML1 that are responsible for Notch activation.

A fusion protein was constructed, consisting of ANTP/DN-MAML (TR4) (FIG. 3B) (SEQ ID NO.:2). The construct was tested for the ability to mediate nuclear translocation, inhibit Notch signaling activation, Biodistributed in animals, and target the outer-, middle- and inner-core of mammary tumors.

Production

ANTP/DN-MAML fusion protein was produced in a bacterial expression system (*E. Coli*). Expression strains of bacteria were transformed with the vector containing the fused genes, the expression was induced, and the bacteria were lysed. Expression of the ANTP/DN-MAML fusion protein was maximal three hours post induction with up to 2.5 mg/L of culture. The fusion protein product was isolated using metal affinity chromatography on a nickel chelating sepharose column under denaturing conditions with guanidinium hydrochloride and urea. The fusion protein product was then refolded with Tris buffered saline before dialysis with PBS twice to give the final functional product. Improperly refolded protein is nonfunctional and precipitates out of the solution. The final yield of 0.8-1 mg of active compound per liter of culture is obtained.

Formulation and Storage

The fusion protein was frozen in PBS at 0.25 mg/mL. Prior to use, the fusion protein was concentrated tenfold to 2.5 mg/mL.

Characterization and Detection

ANTP/DN-MAML is a 14.18 KDa fusion protein of:

a) the 60 amino acid antennapedia homeodomain with a molecular weight of 6.6 KDa (SWISSPROT=P02833)(R K R G R Q T Y T R Y Q T L E L E K E F H F N R Y L T R R R R I E I A H A L C L T E R Q I K I W F Q N R R M K W K K E N) (SEQ ID NO.:4)

b) the 62 amino acid DN/MAML sequence (SWISSPROT=Q92585 (MAML1-HUMAN, amino-acid 13-74)) with a molecular weight of 6.8 KDa (L P R H S A V M E R L R R R I E L C R R H H S T C E A R Y E A V S P E R L E L E R Q H T F A L H Q R C I Q A K A K R A G K H) (SEQ ID NO.:5)

c) a pentahistidine tag for purification with a molecular weight of 0.775 KDa.

Fractions of the ANTP/DN-MAML fusion protein purified from the affinity column were detected by SDS-PAGE with Coomassie blue staining as well as with immunoblotting using anti-pentahistidine antibody, followed by peroxidase-conjugated antibodies.

Example 6

ANTP/DN-MAML-Mediated Nuclear Transduction

To determine the cellular localization of the ANTP/DN-MAML (TR4) fusion protein, immunostaining on human mammary epithelial breast cancer MDA-MB231 cells was carried out. MDA-MB231 cells were cultured to sub-confluence in Dulbecco's modified Eagle's medium containing 10% calf serum at 37° C. The coverslips with cells attached were washed, and incubated with ANTP/DN-MAML purified fusion protein in serum free media for two hours at a concentration of 50 μM. Cells were washed three times and fixed with 4% paraformaldehyde for 15 minutes. After brief washes, the coverslips were incubated with blocking solution and subsequently with anti-His primary and FITC-conjugated secondary antibody. Fluorescence was observed with a Zeiss Axioscope 40 fluorescence microscope.

The results indicate a nuclear localization for ANTP/DN-MAML in adherent cells. This localization is of interest because the human cancer mammary epithelial cell line MDA-MB231 tend to be among the more difficult cells to transfect.

Example 7

ANTP/DN-MAML-Mediated Notch Inhibition

To investigate the potential role of ANTP/DN-MAML to inhibit Notch signaling activation the high metastatic mammary epithelial cell line MDA-MB231 cell line was treated with the ANTP/DN-MAML fusion protein for two hours. Total protein was extracted from cells using SDS buffer. Total protein concentrations were determined using the BCA protein assay kit. Total protein (10-50 g) was diluted in 5× sample buffer (250 M Tris-HCl pH 6.8, 500 mM dithiotheitol, 10% SDS, 0.5% bromophenol blue, 50% glycerol), heated at 100° C. and analyzed by SDS-PAGE. Electrophoresis was carried out in running buffer (25 mM Tris HCl, 250 mM glycine, 0.1% SDS) for 60 minutes or until the bromophenol blue had run out of the gel. Separated proteins were transferred to nitrocellulose membrane in ice cold transfer buffer (39 mM glycine, 48 mM Tris HCl) electrophoretically for 90 minutes at 100V. Western blots were probed with the primary antibody in blocking buffer at 4° C. over night with anti-Mouse IgG peroxidase produced in goat primary antibody (Sigma A9917). Nitrocellulose membranes were washed 4 times for five minutes each in TBS-T buffer. Secondary antibody polyclonal Rabbit anti-goat was diluted in blocking buffer at 1:10,000 and incubated for 60 min at room temperature followed by 4 washes of five min in TBS-T. 2 ml of Super Signal West Pico Chemiluminescent substrate reagent (PIERCE) were used to detect specific binding and signals were captured on Kodak XAR-5 film.

Expression of ANTP/DN-MAML was accompanied by the downregulation of the activated of Notch (NICD) in cells transfected with the ANTP/DN-MAML, but not with ANTP transfected or in parental (untransfected) cells. Downregulation of Notch activation occurred in cells treated with the ANTP/DN-MAML fusion protein, but not in cells treated with ANTP alone. The results indicate that ANTP/DN-MAML can be used to block Notch activation.

Example 8

ANTP/DN-MAML Biodistribution

To determine whether Antennapedia could be used to deliver the DN-MAML in vivo, CD1 nude mice were injected intravenously via tail vein with 4 mg/kg of the ANTP/DN-MAML fusion protein. The mice were perfused for 5 min with phosphate-buffered saline and sacrificed 2 hours following the injection. The expression of ANTP/DN-MAML in each organ was determined by Western blot analysis. Tissue samples from the liver, kidney, heard, lung, spleen, and brain showed a significant signal from ANTP/DN-MAML injected mice as compared to control PBS injected mice. Of interest, ANTP/DN-MAML was also detected in the brains of animals, suggesting that ANTP/DN-MAML can cross the blood-brain barrier. As such, the targeted delivery system of the present invention may have wide applications in the administration of therapeutic proteins to the central nervous system.

Example 9

ANTP/DN-MAML Penetrates the Outer- Middle- and Inner-Core of Mammary Tumors

Purified ANTP/DN-MAML fusion protein was injected into CD1 Nude mice xenografted with MDA MB231 human mammary epithelial breast cancer cells via the tail vein. The mice were perfused for 5 min with phosphate-buffered saline and sacrificed 2 hours following the injection. The tumor was removed and dissected under a stereoscope to separate the outer, middle, and inner core of the tumor. The ANTP/DN-MAML in each core of the tumor was determined by Western blot. Expression of ANTP/DN-MAML was detected in the outer, middle and inner core of the tumor in an animal injected with the ANTP/DN-MAML, but not in a control animal injected with PBS.

In order to establish the localization of ANTP/DN-MAML within the tumors, immunohistochemistry on the above mammary cancer samples was performed. Intense ANTP/DN-MAML staining within the nucleus of mammary cancer cells was observed. These data demonstrate that the ANTP/DN-MAML fusion protein mediates nuclear localization in vivo.

Example 10

In Vivo Tumor Reduction with Antennepedia-Dominant Negative Mastermind

Figure 4A:
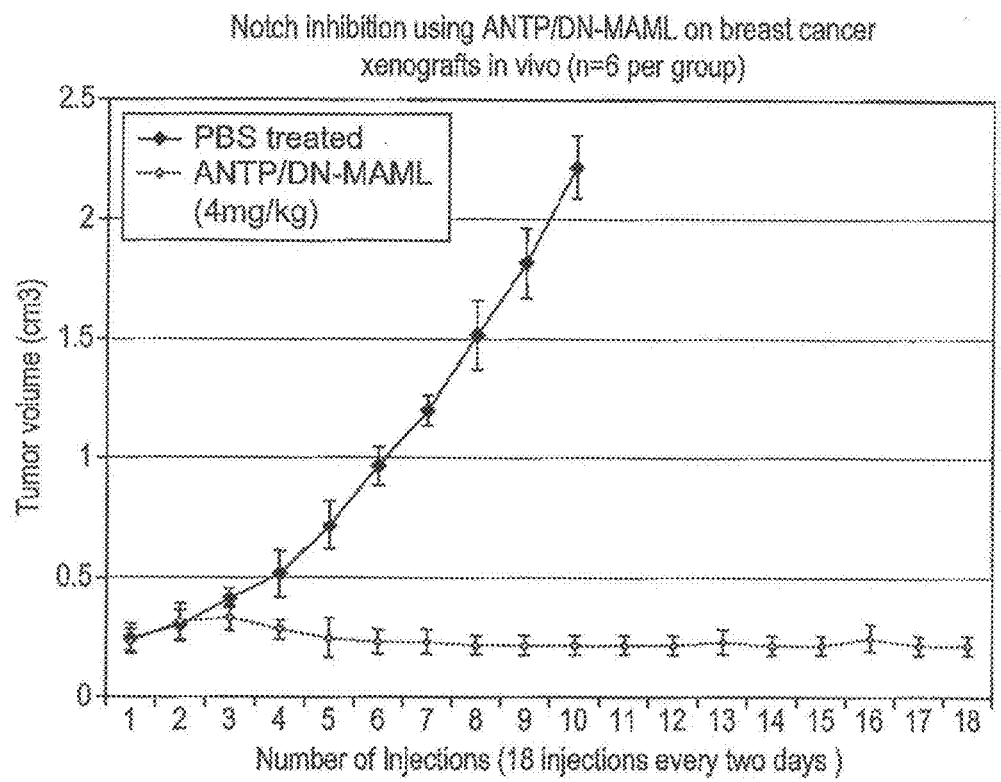
FIG. 4 is a graph depicting (4A) tumor volume of animals treated with ANTP/DN-MAML fusion protein and (4B) animal survival after treatment with ANTP/DN-MAML fusion protein.
Figure 4B:
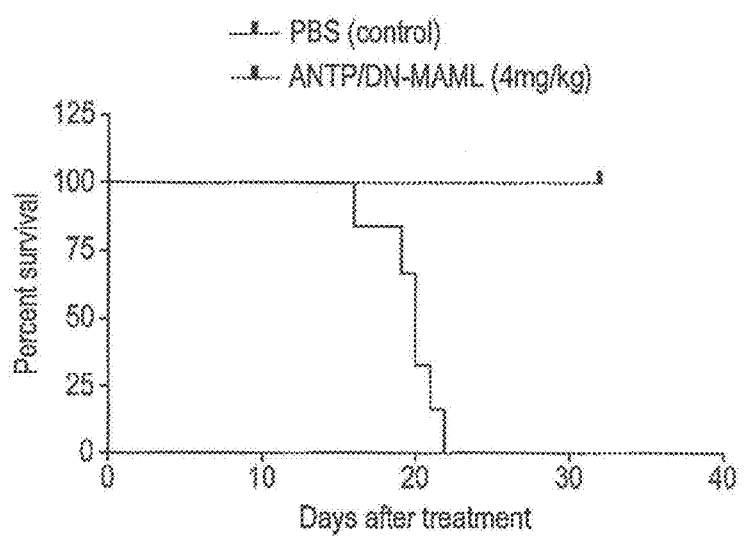

Breast cancer xenografts were established in mice. The mice were divided into two groups, and injected every two days with either PBS as a control, or with 4 mg/kg ANTP/DN-MAML fusion protein (n=6 per group) (FIG. 4A). Control mice treated with PBS developed rapidly growing tumors. The control mice were euthanized after twenty days. Mice treated with ANTP/DN-MAML had no increase in tumor volume after thirty-two days, indicating that ANTP/DN-MAML prevents or suppresses tumor growth. (FIG. 4B).

Example 11

Toxicological and Immunogenic Studies

The following in vivo experiments were undertaken to investigate the safety, immunogenicity, and efficacy of ANTP/DN-MAML in tumor models. Immunogenicity is a measure of the immune response to a therapeutic drug. It is relevant to the use of therapeutic protein drugs because development of anti-drug antibodies can cause allergic or anaphylactic reactions, reduction in drug efficacy, and/or induction of autoimmunity.

The immunogenicity of ANTP/DN-MAML was investigated in immuno-competent mice. Animals were immunized intravenously with ANTP/DN-MAML (0.2 ml, 2.5 mg/ml) without adjuvant, once per day for 5 days. Mice were bled once per week over a 4-month period, and the immune response monitored by ELISA. Blood samples were diluted 1:10, 1:100 and 1:1000 in PBS, and the immune response was monitored by ELISA on native ANTP/DN-MAML (coated at 50 µg/ml) and detected using anti-mouse antibodies. The results indicated that ANTP/DN-MAML does not raise an immune response in immunocompetent mice at a dose of 2.5 mg per week. This dose is equivalent to 100 mg/kg in humans.

Example 12

In Vivo Maximum Tolerated Dose Studies

ANTP/DN-MAML tail vein administration was started when the mice reached an age of 12 weeks. Mice were continuously monitored for signs of hypoglycemic shock or drug side effects and were sacrificed if body weight loss exceeded 15%. Various dosages were tested starting at 4 mg/kg/day. It was found that 57 mg/kg/day of ANTP/DN-MAML is the maximum tolerated dose. At this dose, mice suffered from loss of appetite, weight loss and hypoglycemia. This experiment was terminated by sacrificing the animals three days after injection.

Example 13

Ovarian, Colon, and Pancreatic Cancer Models

High levels of Notch are expressed in colon cancer cells. ANTP/DN-MAML was administered to female nude mice bearing xenografted Colo205 tumors. Injections of 0.2 ml of 4 mg/ml ANTP/DN-MAML protein were administered to the mice every other day. This dose is equivalent to 2 g of ANTP/DN-MAML fusion protein per patient. The results indicated that administration of ANTP/DN-MAML reduced colon cancer cell growth in vivo.

Although the invention has been described with reference to the above examples, it will be understood that modifications and variations are encompassed within the spirit and scope of the invention. Accordingly, the invention is limited only by the following claims.

What is claimed is:

1. A method of determining whether a cancer cell is responsive to treatment by a Notch pathway inhibitory agent wherein the inhibitory agent is a fusion protein comprising a negative regulator of Notch signaling and an Antennapedia homeodomain, the method comprising, (i) administering said Notch inhibitory agent to a cancer cell that has an increased level of Notch 1 as compared to a normal cell and (ii) measuring the level of Notch 1, wherein a lower level of Notch 1 in the cancer cell treated with the Notch inhibitory agent as compared with the level of Notch 1 in a cancer cell not treated with the Notch inhibitory agent is indicative of a cancer cell responsive to treatment by a Notch pathway inhibitory agent.

2. The method of claim 1, wherein the negative regulator of Notch signaling in the Notch pathway inhibitory agent comprises a dominant negative Mastermind isoform or a Numb isoform.

3. The method of claim 1, further comprising determining the level of Numb expression in the cancer cell, wherein a low level of Numb expression as compared with the level in a normal cell, is indicative of a cancer cell responsive to treatment by a Notch pathway inhibitory agent.

4. The method of claim 1, wherein the cancer cell is a breast cancer cell, an ovarian cancer cell, a colon cancer cell, a lung cancer cell, a prostate cancer cell, a hematopoietic cancer cell or a pancreatic cancer cell.

5. The method of claim 1, wherein the Notch pathway inhibitory agent is set forth in the amino acid sequence of SEQ ID NO: 1 or SEQ ID NO: 2.

* * * * *